(12) United States Patent
Montague et al.

(10) Patent No.: US 11,103,718 B2
(45) Date of Patent: Aug. 31, 2021

(54) AUTOMATED EXTERNAL DEFIBRILLATOR DEVICE AND METHODS OF USE

(71) Applicant: EIR Inc., Denver, CO (US)

(72) Inventors: Gary Montague, Denver, CO (US); David Jon Farrell, Loveland, CO (US); James Dotter, Boulder, CO (US); Krista Grandey, Denver, CO (US); James A. Gilbert, Bouder, CO (US); Neil D. Blank, Eldorado Springs, CO (US)

(73) Assignee: HeartHero, Inc., Denver, CO (US)

( * ) Notice: Subject to any disclaimer, the term of this patent is extended or adjusted under 35 U.S.C. 154(b) by 240 days.

(21) Appl. No.: 15/847,826

(22) Filed: Dec. 19, 2017

(65) Prior Publication Data

US 2018/0169426 A1   Jun. 21, 2018

Related U.S. Application Data

(60) Provisional application No. 62/436,208, filed on Dec. 19, 2016.

(51) Int. Cl.
*A61N 1/39*    (2006.01)
*G16H 80/00*   (2018.01)
(Continued)

(52) U.S. Cl.
CPC ......... *A61N 1/39044* (2017.08); *A61H 31/00* (2013.01); *A61H 31/005* (2013.01);
(Continued)

(58) Field of Classification Search
CPC ............ A61N 1/39044; A61N 1/39046; A61N 1/3987; A61N 1/3975; A61N 1/3925;
(Continued)

(56) References Cited

U.S. PATENT DOCUMENTS 5,817,151 A    10/1998   Olson et al.
5,871,505 A    2/1999    Adams et al.
(Continued)

FOREIGN PATENT DOCUMENTS

CN    101745180       6/2010
EP    2450082 A1     5/2012
(Continued)

OTHER PUBLICATIONS

PCT Patent Application PCT/US2017/067442 International Search Report and Written Opinion dated Apr. 19, 2018.
(Continued)

*Primary Examiner* — Tammie K Marlen

(74) *Attorney, Agent, or Firm* — Erise IP, P.A.

(57) ABSTRACT

The present invention relates to a device, and software and methodology associated with a portable Automated External Defibrillator ("AED"). The portable AED works with a mobile device and software, and includes two or more cardiac pads, a battery pack, and specialized capacitor. When connected to a patient in cardiac arrest, the AED contacts Emergency Medical Services, and records patient information to be transmitted for evaluation by medical providers. The AED is able to analyze cardiac rhythms, suggests administering one or more shocks to the patient in appropriate cardiac arrhythmia, and guides a user on proper CPR technique, if enabled. The AED software can alert other personnel via a mobile device app.

6 Claims, 21 Drawing Sheets

(51) Int. Cl.
*G16H 40/63* (2018.01)
*G16H 40/67* (2018.01)
*A61H 31/00* (2006.01)
*A61N 1/04* (2006.01)

(52) U.S. Cl.
CPC ........... *A61N 1/3925* (2013.01); *G16H 40/63* (2018.01); *G16H 40/67* (2018.01); *G16H 80/00* (2018.01); *A61H 2201/0188* (2013.01); *A61H 2201/1619* (2013.01); *A61H 2201/5043* (2013.01); *A61H 2201/5071* (2013.01); *A61H 2201/5084* (2013.01); *A61H 2230/00* (2013.01); *A61H 2230/065* (2013.01); *A61N 1/046* (2013.01); *A61N 1/0492* (2013.01); *A61N 1/3975* (2013.01); *A61N 1/3987* (2013.01); *A61N 1/3993* (2013.01)

(58) Field of Classification Search
CPC .... A61N 1/046; A61N 1/0483; A61N 1/3993; A61N 1/0492; G16H 40/67; G16H 40/63; G16H 80/00; A61H 31/00; A61H 31/005; A61H 2201/0188; A61H 2201/1619; A61H 2201/5043; A61H 2201/5071; A61H 2201/5084; A61H 2230/00; A61H 2230/065

See application file for complete search history.

(56) References Cited

U.S. PATENT DOCUMENTS

| | | | |
|---|---|---|---|
| 5,908,443 A | 6/1999 | Brewer et al. | |
| 6,353,758 B1 | 3/2002 | Gliner et al. | |
| 6,456,877 B1 | 9/2002 | Fishler | |
| 6,539,255 B1 | 3/2003 | Brewer et al. | |
| 8,615,295 B2 | 12/2013 | Savage et al. | |
| 10,226,615 B2 | 3/2019 | Lang et al. | |
| 10,799,709 B2 | 10/2020 | Teber et al. | |
| 2004/0143297 A1 | 7/2004 | Ramsey | |
| 2004/0260376 A1 | 12/2004 | Craige et al. | |
| 2005/0244709 A1 | 11/2005 | Bucher | |
| 2007/0032830 A1 | 2/2007 | Bowers | |
| 2007/0218869 A1* | 9/2007 | Thijs | G08B 27/001 455/404.2 |
| 2007/0299473 A1* | 12/2007 | Matos | A61N 1/0476 607/5 |
| 2009/0240297 A1 | 9/2009 | Shavit et al. | |
| 2009/0254136 A1* | 10/2009 | Powers | A61N 1/3993 607/5 |
| 2010/0241181 A1 | 9/2010 | Savage et al. | |
| 2011/0071880 A1 | 3/2011 | Spector | |
| 2011/0152702 A1 | 6/2011 | Goto | |
| 2011/0190839 A1 | 8/2011 | Vaisnys et al. | |
| 2011/0224745 A1 | 9/2011 | Magruder | |
| 2012/0310315 A1 | 12/2012 | Savage et al. | |
| 2013/0012151 A1 | 1/2013 | Hankins | |
| 2013/0132465 A1 | 5/2013 | Brown | |
| 2014/0004814 A1 | 1/2014 | Elghazzawi | |
| 2014/0039593 A1 | 2/2014 | Savage et al. | |
| 2014/0107718 A1 | 4/2014 | Foote et al. | |
| 2014/0277227 A1 | 9/2014 | Peterson et al. | |
| 2014/0317914 A1 | 10/2014 | Shaker | |
| 2016/0220833 A1 | 8/2016 | Qing et al. | |
| 2016/0271408 A1* | 9/2016 | Newton | A61N 1/3904 |
| 2017/0157415 A1 | 6/2017 | Horseman et al. | |
| 2019/0329057 A1 | 10/2019 | Teber et al. | |
| 2020/0398066 A1 | 12/2020 | Teber et al. | |

FOREIGN PATENT DOCUMENTS

| | | |
|---|---|---|
| EP | 3506981 A1 | 7/2019 |
| EP | 3506981 A4 | 12/2019 |
| JP | 2020524058 A | 8/2020 |
| WO | 2001010496 A2 | 2/2001 |
| WO | 2007069162 A1 | 6/2007 |
| WO | 2007135599 A2 | 11/2007 |
| WO | 2008057302 A2 | 5/2008 |
| WO | 2010146492 A1 | 12/2010 |
| WO | 2015143460 A1 | 10/2015 |
| WO | 2016092800 A1 | 6/2016 |
| WO | 2016149680 A1 | 9/2016 |
| WO | 2018232450 A1 | 12/2018 |

OTHER PUBLICATIONS

Automated External Defibrillators—New AEDs-AED.com, www.aed.com/new-aeds.html. Retrieved Sep. 14, 2018.
How Corpuls Works, Always Very Close to the User, https://corpuls.world/, Copyright 2017, Retrieved Sep. 14, 2018.
Heartsmart.com, Defibtech Lifeline AED, www.heartsmart.com/defibtech-lifeline-aed-defibrillator-p/dcf-100.htm, Copyright 2015, Retrieved Sep. 14, 2018.
Schiller the Art of Diagnostics, The World's First Pocket Defibrillator Fred Easyport, www.schiller.ch/ca/us/product/fred-easyport, Retrieved Sep. 14, 2018.
Phillips, HeartStart FRx Automated External Defibrillator, www.usa.philips.com/healthcare/product/HC861304/heartstart-frx-automated-external-defibrillator, Copyright 2004-2018, Retrieved Sep. 14, 2018.
Phillips, HeartStart OnSite AED, Product No. M5066A, www.usa.philips.com/healthcare/product/HCM5066A/heartstart-onsite-aed, Copyright 2004-2018, Retrieved Sep. 14, 2018.
Physio Control, Product Overview, www.physio-control.com/ProductsPrehospital.aspx, Copyright 2018, Retrieved Sep. 14, 2018.
Extended European search report (EESR) dated Jul. 10, 2020.
"AED Plus Technical Specifications", Dec. 31, 2011; Retrieved from the Internet: URL:https://web.archive.org/web/20120526132350if_/http://zoll.com/uploadedFiles/Public_Site/Products/AED_Plus/AED PlusSpecSheet.pdf; Retrieved on Jun. 30, 2020.
Okamura et al, "Evaluation of a Unique Defibrillation Unit with Dual-Vector Biphasic Waveform Capabilities: Towards a Miniaturized Defibrillator", Pace, Published Feb. 2017, pp. 108-114, vol. 40.
Dames, J.S., "Monophasic vs Biphasic Waveform Defibrillation," AED Superstore Website, published on Mar. 3, 2016 [online], retrieved from <URL:https://www.aedsuperstore.com/resources/monophasic-vs-biphasic/ [retrieved on Aug. 14, 2019], 9 pages.
Cahn, Michelle, "Connecting Your IoT Platform to 911: RapidSOS Emergency API," RapidSOS Website, published on Oct. 24, 2017 [online], retrieved from <URL:https://rapidsos.com/our-latest/product-spotlight-rapidsos-emergency-api/ [retrieved on Mar. 12, 2021], 3 pages.

* cited by examiner

AUTOMATED EXTERNAL DEFIBRILLATOR DEVICE AND METHODS OF USE

CROSS REFERENCE TO RELATED APPLICATIONS

The present invention claims the benefit of U.S. Provisional Patent Application No. 62/436,208, filed Dec. 19, 2016, and entitled, "Automatic External Defibrillator Device And Methods Of Use," which is incorporated herein by reference in its entirety.

FIELD OF THE INVENTION

The present invention relates generally to Automated External Defibrillator (AED) and use thereof.

BACKGROUND OF THE INVENTION

There are 395,000 Out of Hospital Cardiac Arrests (OHCA) that occur each year in the United States. Studies have shown that the use of an Automated External Defibrillator (AED) can increase the rate of survivability of OHCA by 40%. However, only 2% of OHCA will occur at a location at which an AED is available. While there is a big push to increase dissemination of Public Access Defibrillators (PAD), research has also shown that 80% of OHCA happen in the home, where the majority of people do not have access to an AED.

Additionally, studies have shown that Sudden Cardiac Arrest (SCA) patients have improved outcomes when the length of time between incident and shock is reduced. When an AED is not readily available at the location at which the OHCA occurs, the time from incident to shock is dependent upon the timely arrival of Emergency Medical Services (EMS). The national average for time of EMS arrival is 9 minutes and, during these 9 minutes, the chance of patient survival decreases by 7-10% every minute. Consequently, SCA patients are more likely to survive with favorable outcomes if the EMS response time is within 8 minutes.

There are three time-sensitive stages of cardiac arrest: 1) electric phase (up to 4 minutes following cardiac arrest, during which the heart is most receptive to electrical shock); 2) circulatory phase (approximately 4 minutes to 10 minutes following cardiac arrest); and 3) metabolic phase (extending beyond approximately 10 minutes following cardiac arrest). Studies using wearable cardioverter defibrillators have shown that addressing cardiac arrest during the initial electric phase results in a 98% first time cardioversion success rate. As a result, rapid administration of an AED treatment to the SCA patient during the electrical phase has shown success with survival rates as high as 74%.

Currently, SCA is a leading cause of death among adults over the age of 40 in the United States and several other countries. In the U.S. alone, approximately 326,200 people of all ages experience out-of-hospital non-traumatic SCA each year, and nine out of ten of these victims die as a result. There are a number of AED solutions for the defibrillation of the lethal arrhythmias suffered by SCA patients. While some of these solutions attempt to make the AED more portable, they fail to meet the needs of the user because they are still cumbersome and heavy, thus are not truly portable devices. For example, the lightest AED currently available on the market is 2.5 pounds, making carrying an AED on-person unlikely. Other products attempt to assist the bystander by prompting them in giving quality CPR, although these products still have shortcomings. Studies show that decreasing the time-to-shock can greatly increase the chance of patient survival, such that four out of ten SCA patients survive when bystanders intervene by giving CPR and using an AED before the arrival of EMS personnel. Unfortunately, only one-third (32%) of SCA patients receive bystander CPR, and bystanders treat only 2% of those with AEDs. If bystanders had a readily available AED that could also shorten the time to EMS notification, analysis of cardiac rhythm, and delivery of shock, potentially 100,000 people per year could be saved in the U.S. alone.

SUMMARY OF THE INVENTION

In accordance with the embodiments provided herein, there is provided a method for performing cardiac defibrillation with a portable automated external defibrillator (AED). The method includes initiating a cardiac defibrillation program on a control module communicative with an electrode pad, and detecting a patient's cardiac rhythm from the electrode pad. The method further includes connecting the control module to a mobile device, executing a call with emergency services, gathering geolocation information, and channeling the call to the emergency services on an audible speaker. The method also includes prompting a user to initiate cardiopulmonary resuscitation (CPR) if the cardiac rhythm is not detected, displaying instructions for CPR on the control module. The method continues with analyzing the patient's cardiac rhythm and notifying the user and emergency services when a shockable cardiac rhythm is detected, and notifying the user to halt CPR. The method also includes shocking the patient, analyzing the patient's cardiac rhythm for a normal pulse, and resuming instructions for CPR if the normal pulse is not detected.

In another embodiment, a compact, automated external defibrillator (AED) system is disclosed. The system includes an electronics module, which in turn includes a power source and electronic circuitry for generating, storing, and dispensing electrical charge from the power source, the electrical charge being suitable for at least one electrical shock to be applied to a sudden cardiac arrest (SCA) patient. The electronics module also includes a display for providing guidance to a user of the system, including instructions on using the system, and firmware for controlling the electronic circuitry and the display. The system also includes at least two cardiac pads, electrically connected with the electronics module and configured for external attachment to the SCA patient so as to transfer the at least one electrical shock from the electronics module to the SCA patient, wherein the power source is a household battery. In an embodiment, the dimensions of the system is less than approximately 8-inches by 6-inches by 3-inches. In another embodiment, the power source is a commonly-available household battery, such as a 9V battery or a plurality of CR123 batteries. In still another embodiment, each of the cardiac pads includes at least one sensor for measuring a patient cardiac rhythm and a body impedance of the SCA patient onto whom the cardiac pads have been attached, and wherein a firmware is configured for automatically adjusting the waveform characteristics of the electrical shock in accordance with the measured body impedance. In yet another embodiment, the system includes a bracket for housing the electronics module and the cardiac pads when the system is not in use. The bracket is configured for sensing at least one of: 1) when the electronics module is removed from the bracket; 2) when the power source is below a preset minimum power threshold; and 3) when the system requires servicing.

In a further embodiment, a method for using a compact AED system is disclosed. The system includes an electronics module and at least two cardiac pads housed in a bracket. The method includes initializing the system by removing the system from the bracket, contacting emergency medical services (EMS), attaching the cardiac pads on a sudden cardiac arrest (SCA) patient, and measuring at least a patient cardiac rhythm and a body impedance of the SCA patient using sensors included in the cardiac pads. The method further includes performing an AED administration protocol on the SCA patient, if so indicated by guidance from the electronics module, and continuing to monitor the patient cardiac rhythm of the SCA patient and following additional guidance from the electronics module until the arrival of EMS personnel.

While certain embodiments are described in terms of specific embodiments, it is to be understood that the invention is not limited to these disclosed embodiments. Many modifications and other embodiments of the invention will come to mind for those skilled in the art to which this invention pertains, and which are intended to be and are covered by both this disclosure and the appended claims. It is indeed intended that the scope of the invention should be determined by proper interpretation and construction of the appended claims and their legal equivalents, as understood by those of skill in the art, relying upon the disclosure in this specification and the accompanying drawings.

Embodiments of the present invention now will be described more fully hereinafter with reference to the accompanying drawings, which are intended to be read in conjunction with both this summary, the detailed description and any preferred and/or particular embodiments specifically discussed or otherwise disclosed. The invention may, however, be embodied in many different forms and should not be construed as limited to the embodiments set forth herein; rather, these embodiments are provided by way of illustration only and so that this disclosure will be thorough, complete and will fully convey the full scope of the invention to those skilled in the art.

DETAILED DESCRIPTION

Figure 1:
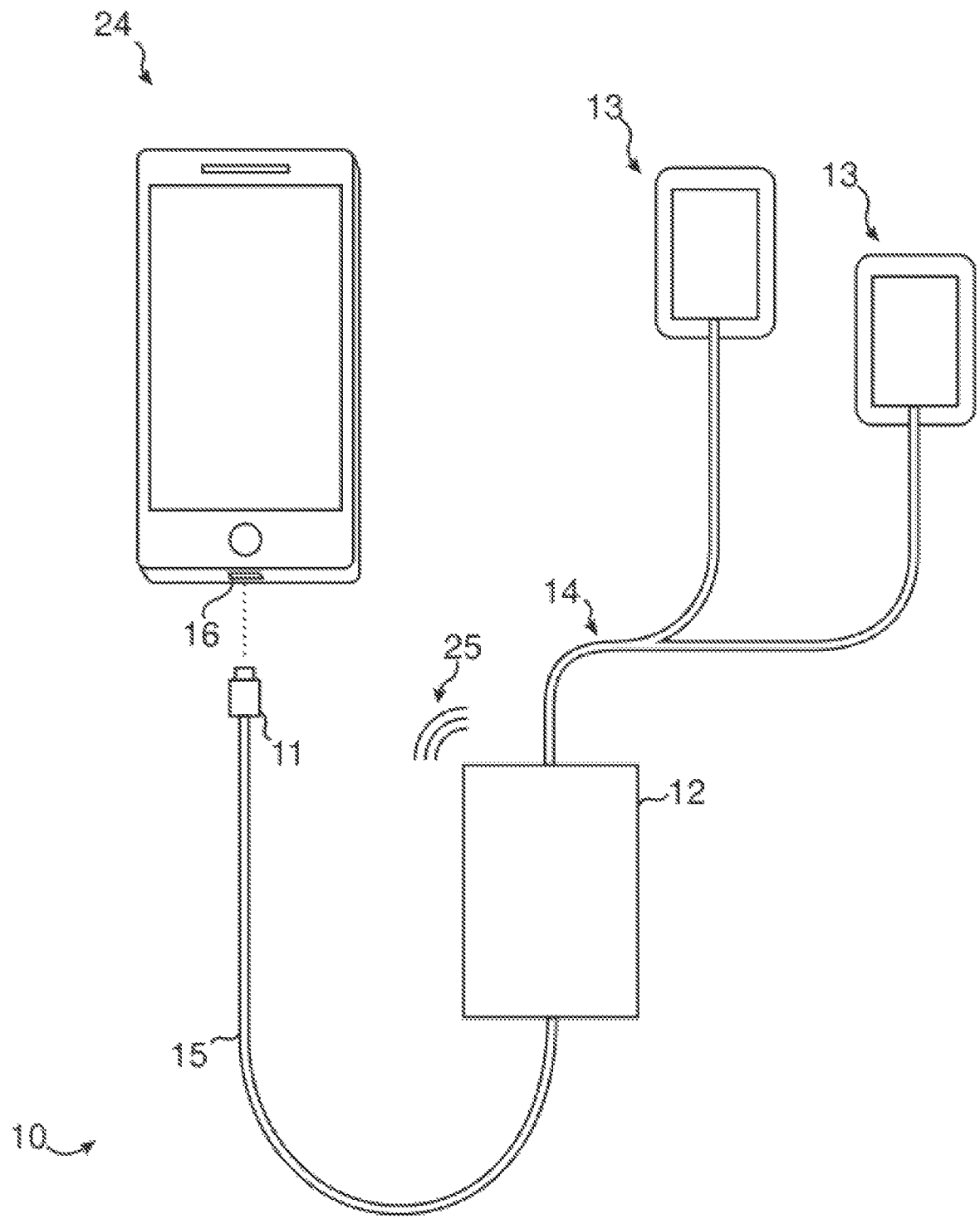
FIG. 1. An automated external defibrillator (AED) module, in accordance with an embodiment.

The present invention seeks to solve the problems described in the Background by providing an AED device with improved features over the existing products. For instance, as correct positioning of the cardiac pads has been correlated with improved survival rates, it would be desirable for an AED to provide an indication of whether the cardiac pads have been placed correctly on the SCA patient. Also, currently available AED devices do not provide an option to connect to a mobile device that can contact EMS to initiate a faster response by emergency medical personnel and, subsequently, earlier hospital arrival. Moreover, currently available AED devices do not provide a smartphone/mobile device application for the notification and treatment of suspected cardiac arrest instances to EMS.

It would be desirable to have a device that can significantly improve the outcome of an SCA patient by providing, even to a non-medically trained person, the ability to detect a shockable cardiac rhythm and apply a therapeutic electrical shock to the SCA patient. Therefore, there currently exists a need in the industry for a truly portable AED and associated methodology that closes the gap between time of incident, application of CPR, and delivery of shock.

To address the aforementioned shortcomings of the existing art, certain embodiments of the system described herein provides a compact Automated External Defibrillator and smartphone device application that assists in the notification of suspected cardiac arrest to Emergency Medical Services and assists in guiding bystander CPR and arrhythmia conversion.

Certain embodiments of the invention further include a smartphone device with associated application software. Alternatively, the smartphone device or a control module allows for cardiac monitoring, vital signs monitoring, defibrillation, and telecommunications that to enable GPS-specific contact with emergency services.

An exemplary embodiment of the AED includes: (1) a defibrillator including a battery to charge a capacitor to store and deliver an electric shock; (2) a communication module to connect the defibrillator to a smartphone/mobile device via wired or wireless connection; (3) cardiac pads with electrodes to detect and monitor chest wall compression depth, compression rate, and chest wall impedance, and heart rhythm; and (4) a smartphone or mobile device application to analyze information received from the cardiac pads and recommend appropriate therapy, the application also having the ability to contact EMS via the smartphone/mobile device with GPS, Wi-Fi and/or cellular capabilities. In certain embodiments, these components are connected as follows: a smartphone with application is connected to the defibrillator via either a wired or wireless connection, such as Bluetooth or Wi-Fi, then at least two electrodes with wires ending in cardiac pads connect from the battery/capacitor pack to the patient's chest.

Certain embodiments include one or more of the following: (1) the smartphone application installer resides in the battery pack and is automatically uploaded to any device connected thereto; (2) device connects to a smartphone or mobile device via a wired or wireless connection (e.g., Bluetooth, Wi-Fi), or through a microphone; (3) the charge for the defibrillating shock is generated from a replaceable device-centric source (e.g., battery) or from the internal battery of the smartphone; (4) device includes a control module, at least one capacitor and application to detect and deliver any range of electrical shock; (5) the system components and application detect the impedance of the victim's chest wall and cardiac pad placement; (6) given impedance information, the system and application automatically recommends or configures an electrical charge for the given SCA patient (e.g., child or adult); (7) the cardiac pads can be placed anywhere on the body of the SCA patient; (8) the cardiac pads detect the force of the CPR compressions on the SCA patient using, for example, a pressure sensor, impedance detector and/or accelerometer; (9) the smartphone interfaces with multiple other medical devices via wired or wireless connections (e.g., Bluetooth or Wi-Fi) or microphone; (10) the application monitors a variety of sources of data to: A) refine CPR-related guidance and/or B) bundle the data to be accessible by first responders; (11) the smartphone interfaces with other medical devices and detects and monitors vital signs on the SCA patient including, but not limited to, blood pressure, heart rate, oxygen saturation, temperature, respiratory rate, capnography, and electrical cardiac activity; (12) the device has two or more electrodes (e.g., cardiac pads) that connect to the patient; (13) the smartphone/device/electrode combination provide a 12-lead electrocardiography (ECG) output; (14) the AED is brand agnostic with respect to the smartphone or operating system; (15) the smartphone can be paired via wireless communications or connect via wire to multiple medical devices simultaneously; (16) the AED can be connected/paired to multiple smartphones simultaneously and, if paired, each of these devices can have control over the AED; (17) the device allows the user to perform cardiac pacing/synchronized shock from the smartphone device, if the user has the appropriate knowledge; (18) the smartphone provides a live video, voice, data or any combination of these feeds to another medical facility; (19) the smartphone communicates with EMS via an automated voice annunciation via cellular network, video, SMS or any other modality by which EMS is able to receive information; (20) information given to EMS includes, but is not limited to, current vital signs, CPR results, detectable cardiac rhythm, number of shocks given, and GPS coordinates/geolocation of events in progress; (21) such information is generated on a periodic basis and transmitted to incoming EMS, or generated upon request by EMS via the application; (22) EMS is able to access the application on a paired mobile device, facilitating device location and data requests therefrom; (23) the application allows the control module to be paired with the information system used by EMS, thus allowing the remote administration of cardiac shock (e.g., if a child is using the device for an adult); (24) the device and software application communicates with cameras of related devices including, for example, smartphone cameras, Google Glass, or similar products to allow for direct visualization and display of events and instructions in progress; (25) the device and software application guides a user for proper cardiac pad placement; (26) the device and software application suggest confirmation of no pulse if the onboard photo-plethysmography (PPG) sensor does not detect a pulse; (27) the device provides guidance using industry standard for timing of delivery of shock and CPR; and (28) device automatically contacts EMS if no call to emergency services is manually initiated after delivery of first shock.

Certain embodiments differ from other currently available devices and solutions because the various embodiments described herein: (1) provide defibrillation of a cardiac arrest victim with an empowered smartphone; (2) use batteries that can be purchased off-the-shelf; (3) include specialized capacitors and circuitry that generate a therapeutic charge from the off-the-shelf battery; (4) continuously analyze the cardiac rhythm during CPR; (5) include sensors in the cardiac pads to detect impedance of the chest wall and ensure proper pad connection; (6) include additional sensors in the cardiac pad to monitor compression force, rate and depth of CPR; (7) by using the sensors to monitor vital signs, ensure that a cardiac shock is not given at an undesired time; and (8) via the sensors inside the cardiac pad, communicate information to the software system regarding size of chest wall which then allows for recommendation of a therapeutic shock that is correlated with the size of victim and their individual anatomy, e.g., child or adult.

Similarly, the associated method described herein differs from existing methods in that: (1) the smartphone software application gives the ability to call emergency services (such as 911 in the United States) and assist the bystander in providing effective CPR; (2) the smartphone device software application is able to upload and record data of the resuscitation efforts such as, but not limited to, vital signs, cardiac rhythm, quality of CPR, and outcome of electric shock. Certain embodiments also transmit data to another mobile device in real-time, or after the fact.

Certain embodiments of the present invention differ structurally from other known devices or solutions in that: (1) the device runs off of readily commercially available consumer batteries; (2) the device connects to a mobile device and is small enough for everyday portability; and (3) includes cardiac pads that can detect force, rate, and depth of compression along with impedance of chest wall.

Furthermore, the processes associated with certain embodiments of the invention differ from known processes and solutions in that: (1) the device includes a smartphone device software application initiate communications with EMS; (2) the software application guides a bystander through quality CPR using the data obtained from the cardiac pads, such as compression depth, compression rate, and placement of hands; (3) the device uses the data to prompt the user if the cardiac pads need to be checked or re-applied or if the CPR technique needs to be modified; (4)

software application detects the cardiac rhythm during active chest compression; (5) the software application analyzes cardiac rhythm and provides electric shock for appropriate cardiac arrhythmias; and (6) the user will be prompted to stop CPR upon return of spontaneous circulation (ROSC).

Among other things, it is an object of certain embodiments of the present invention to provide an automated external defibrillator and smartphone device application that assist in the notification of suspected cardiac arrest to EMS and in guiding bystander CPR and arrhythmia conversion to overcome the problems or deficiencies associated with prior solutions.

It is still further an objective of certain embodiments of the present invention to create a automated external defibrillator device that is cost effective, thus increasing the public's access to AEDs and thereby saving lives.

Further still, it is an objective of certain embodiments of the present invention to provide a device that is smaller and more lightweight than other solutions, thereby enabling the device to be easily portable. Certain embodiments have a weight of less than one pound. By making it more portable it increases accessibility, thus the product will be utilized more frequently, ultimately saving more lives.

Further still, it is an objective of certain embodiments of the present invention to create a device that is able to help bystanders in a high stress situation to provide proper help in an efficient manner.

Certain embodiments of the invention are related to automated external defibrillator and smartphone device software application that assist in the notification of suspected cardiac arrest to EMS and assist in guiding bystander CPR and cardiac arrhythmia conversion.

Certain embodiments include: a smartphone/mobile device, external battery pack/specialized capacitors, at least two cardiac pads and sensors with associated wires. In an embodiment, these components are connected as follows: mobile device is connected via hardwire, Bluetooth or Wi-Fi to a case that holds the battery, specialized capacitors, and circuitry. The case also holds at least two cardiac pads with sensors connected via wire, that are in turn connected to the patient. In an exemplary embodiment, the case protects the user from the risk of electrical shock, and protects the internal electronics from electrostatic discharge (ESD), which can cause the electronics to fail or malfunction in an unsafe way. Suitable materials for the case includes, for example, a variety of plastics and other insulating materials.

Connecting the various components to the mobile device is done via wire to a connection port on the mobile device or via a wireless mechanism such as Bluetooth or Wi-Fi. The mobile device includes software for receiving input via wire or wireless connection from the case and other vital sign attachments. The software can recommend initiating a call to emergency services (e.g., 911). The automated connection via cellular network, video or SMS to EMS will be able to disclose the location of the AED being operated. The device and software can automatically send the patient's information including, but not limited to, vital signs and cardiac rhythm to the EMS dispatch and/or regional medical center. The automated system can guide the user regarding correct depth and rate of compression and be able to advise cardiac shock. The case holds a portable battery, capacitors, and circuitry to generate and store at least one electrical charge to produce a therapeutic charge to cardiovert a patient in cardiac arrhythmia with the goal of return of spontaneous circulation (ROSC). The cardiac pads are connected to the to the case via hardwires. The cardiac pads are able to detect cardiac rhythm when active CPR is taking place. As an example, the cardiac pads have sensors embedded that will be able to detect rate and depth of compressions of the bystander providing CPR. The sensors in the cardiac pads send information back to the mobile device application for analysis of shockable versus non-shockable cardiac rhythm. The cardiac pads are used to deliver the therapeutic shock to the heart. The cardiac pads detect impedance of the chest to allow the application to calculate the correct therapeutic electric shock dosage and also ensure the cardiac pads have the proper connection on the patient to increase the best chance of cardioverting.

In certain embodiments, the method includes: identifying a person, who is the victim of a suspected cardiac arrest; deploying a portable automated external defibrillator device; connecting the portable defibrillator device to a mobile using a wired or wireless connection; automatically initiating the software to prompt the user to call to EMS by screen button prompt; selecting an option on the screen of the mobile device to initiate a call to EMS; and advising EMS of the AED's current location using the mobile device's internal GPS system and request that help be sent once connected. In certain embodiments, a user opens cardiac pads and places them on the victim's chest in either the anterior/posterior placement or the anterior lateral placement described on a packing diagram provided on the case of the AED. As soon as the cardiac pads are placed on the victim's chest, the system attempts to detect and analyze the cardiac rhythm of the victim. Concurrently, the software gives voice prompts and a visual display of how to perform CPR to the user. The software also recommends hand placement, compression depth, and compression rate for effective quality CPR, in accordance with American Heart Association guidelines. As soon as a shockable rhythm is identified, the system will prompt via voice and video display to halt the CPR to initiate a shock to the victim. Once shock is delivered, the system will prompt the user to resume the proper steps of CPR. The device can also display the patient's vital signs on a screen during the time the device is deployed. The vital signs and cardiac rhythm can also be seen by other mobile devices and/or the emergency service dispatch or regional medical center. If at any time the sensors on the cardiac pads detect that CPR is not given at the appropriate rate or compression depth recommended by American Heart Association (AHA) guidelines (see, for example, "AED Implementation" (http://cpr.heart.org/AHAECC/CPRAndECC/Programs/AED-Implementation/UCM_473198_AE D-Implementation.jsp, accessed 18 Dec. 2017)), the software prompts the user by voice and video image to adjust accordingly. The sensors also prompt the user if impedance is too high and recommend checking and/or reattaching the cardiac pads as necessary. Data regarding the entire event can be monitored and saved to another device or to the active device for real-time or subsequent comparative analysis.

Certain embodiments relate to a device, proprietary software and methodology associated with the device. With respect to certain embodiments, the present invention includes a portable defibrillator that works with a smartphone and software. When connected to a patient in cardiac arrest, via two or more electrodes and battery pack/specialized capacitor calls Emergency Medical Services providing a location. It will record patient information such as cardiac rhythm and vital signs that can then be transmitted to an approved facility for evaluation by medical providers. The device is also able to analyze cardiac rhythms, suggests administering one or more shocks to the patient in appropriate cardiac arrhythmia, and instructs bystanders on proper CPR. The portable defibrillator device and software can alert any other personnel with the app downloaded in a nearby location for assistance. This device can be used for any person that is believed to be in cardiac arrest by bystanders. The components of the invention include an application for smartphone, a device that is connected to the smartphone and activates software, the device includes two or more electrodes with cardiac pads for connection to a person's chest and to a battery pack and capacitor to provide electric shocks. In certain embodiments, the configuration includes: a smartphone which is connected by wire to battery pack and capacitor which are connected to electrodes that are connected to cardiac pads that are placed on the chest of the patient.

With respect to certain embodiments of the device AED module, it should be further noted that once the device has been applied to patient and plugged into the smartphone it will activate the software that will transmit location, vital signs, and cardiac rhythm to emergency services, it will also analyze placement of the cardiac pads to ensure proper rhythm analysis and proper CPR via depth, rate and impedance. Device will recommend administering electric shock to appropriate and susceptible cardiac arrhythmias. If the device is used properly and there is a shockable rhythm the goal is the return of spontaneous circulation (ROSC), activation of emergency medical services and recording and transmission of data that occurred during event. With respect to the associated method, in certain embodiments, the method includes: identifying a patient that may have cardiac arrest; placing a device and plugging into smartphone; accessing a smartphone application; following instructions from device and deliver shock if recommended or provide CPR if recommended and wait for emergency services to arrive. Ultimately, at the conclusion of these steps the device should notify emergency services if cell or Wi-Fi signal allows, provide instructions for CPR or recommend and deliver cardiac shock, record vital signs and cardiac rhythm, with the all-encompassing goal of helping bystanders provide emergent and adequate care in a life-threatening situation. A portable AED will lead to improved patient outcomes and more lives being saved.

Referring to the figures, FIG. 1 shows an automated external defibrillator (AED) module 10, in accordance with an embodiment. As seen in FIG. 1, AED module 10 includes a connector 11, an electronics module 12, at least two electro-conductive cardiac pads 13, and electrical conductors such as wiring 14 connecting cardiac pads 13 with electronics module 12. Cardiac pads 13 includes sensors (not shown) for monitoring, for example, cardiac rhythm and body impedance of the SCA patient to whom cardiac pads 13 are connected. The sensors in cardiac pads 13 also indicates whether cardiac pads 13 are properly placed on the SCA patient, and can indicate to electronics module 12 if one or both of cardiac pads 13 are disconnected from the SCA patient. Furthermore, sensors in cardiac pads 13 can also include additional capabilities, such as detection of force, rate, and depth of compression, to help monitor any cardiopulmonary resuscitation (CPR) performed on the SCA patient. Connector 11 is attached to electronics module 12 via a wire 15 in the embodiment shown in FIG. 1. Alternatively, the connection between the mobile device and electronics module 12 is established wirelessly through, for instance, Bluetooth or Wi-Fi. Connector 11 is attached via a receptacle 16 to a mobile device 24.

While mobile device 24 in FIG. 1 is shown as a smartphone, it may be another suitable portable device, such as a cellphone, a tablet, a smart watch, electronic reader, laptop, or the like. A suitable mobile device has the capability to receive input via, for example, wired or wireless connections such as Bluetooth, audio, keyboard, mouse, trackpad, or touch-screen. Additionally, the mobile device produces an output, such as vibration, camera light, video display Bluetooth, Wi-Fi, or audio. Internal components of a suitable device include, for example, a microprocessor, a battery, GPS, Wi-Fi and/or Bluetooth, an operating system, software readable media, and storage. When mobile device 24 is connected with AED module 10, a specialized application software, including features such cardiac rhythm recognition, patient monitoring, impedance measurement, and external communication options, is downloaded and installed on mobile device 24 such that it is able to communicate with AED module 10.

AED module 10 connects to receptacle 16 of mobile device 24 via connector 11, in the embodiment shown in FIG. 1. Certain embodiments include standard connection mechanisms known to those skilled in the art, such as but not limited to micro USB, Lightning connector, and USB-C, 30-pin, Thunderbolt, audio, or even simultaneous connections with multiple inputs of mobile device 24. Alternatively, AED module 10 connects to mobile device 24 wirelessly (as indicated by symbol 25) via a mechanism such as Bluetooth, Wi-Fi, or audio. Connector 11 receives and sends signals from and to electronics module 12, such as communications related to, for instance, activation of the specialized software application, the cardiac rhythm analysis, and delivery of a therapeutic shock.

In certain embodiments, AED module 10 automatically activates the specialized software application installed on mobile device when connector 11 is connected to mobile device 24 via receptacle 16. For instance, the installed software on mobile device 24 analyzes the cardiac rhythm from cardiac pads 13 that is processed/filtered in electronics module 12. Alternatively, electronics module 12 performs the analysis of data received from cardiac pads 13 and displays the analysis results on mobile device 24. Electronics module 12 generates and stores an electrical charge for at least one electrical shock. If electronics module 12 or the installed software in mobile device 24 deems the patient is currently undergoing cardiac arrest and can be treated with defibrillation, a control circuitry (not shown) in electronics module 12 sends the generated electrical charge to the SCA patient via cardiac pads 13. Alternatively, shock will be delivered when the user approves the shock delivery through the specialized software installed on mobile device 24.

In an embodiment, each of cardiac pads 13 is configured to accommodate electrical charge in the form of a biphasic waveform, as currently recommended by Advanced Cardiovascular Life Support (ACLS) and American Heart Association (AHA) standards. Cardiac pads 13 can be placed in the standard anterior/lateral position, or can be placed into the anterior/posterior position, among others.

In an embodiment, electronics module 12 itself or the specialized software on the mobile device will analyze the electrocardiography (ECG) signals received via the sensors in cardiac pads 13. The analysis determines, for example, whether the cardiac rhythm measured from the SCA patient is indeed a shockable rhythm, in accordance with industry standards. Industry standard shockable rhythms include, for example, ventricular fibrillation (VF) having an average waveform amplitude greater than 0.2 mV, fine ventricular fibrillation (FVF) having an amplitude between 0.1 mV and 0.2 mV, and ventricular tachycardia (VT) of single morphology (monomorphic VT) or several morphologies (polymorphic VT) (see, for example, "AED Algorithm Application Note," Philips, 2008 (http://laerdalcdn.blob.core.

windows.net/downloads/f2374/AED_algorithm_application_note.pdf accessed 10 Dec. 2017).

When analysis by electronics module 12 or the software installed on mobile device 24 determines that the cardiac rhythm detected is a shockable rhythm, data regarding body impedance is used to calculate and adjust the appropriate shock waveform to be delivered via cardiac pads 13 to the SCA patient. For instance, the energy output from electronics module 12 is adjusted, according to the body impedance, to produce a waveform according to the accepted standard biphasic pattern used in modern defibrillators. In certain embodiments, this voltage waveform is generally between 120-200 Joules in total energy.

In certain embodiments, the analysis performed by electronics module 12 or software provides an optional mode in which rhythms requiring an electrical shock at a smaller/different electrical output can be identified. An example for such a rhythm is supraventricular tachycardia (SVT), which requires therapeutic cardioversion or bradycardia with external electrical cardiac pacing. In an embodiment, electronics module 12 or software on mobile device 24 is able to distinguish the need for a synchronized shock to be delivered on the QRS waves of an ECG reading. Examples of these rhythms would be supraventricular tachycardia (SVT), stable ventricular tachycardia, symptomatic atrial fibrillation and others.

In certain embodiments, for further data input for the shockability analysis, additional electrodes can be placed in the industry standard positions to obtain, for instance, a 12-lead ECG reading. With this option, the 12-lead ECG data allows better analytics of the SCA patient's condition, such as the identification of a ST elevation myocardial infarction (STEMI). For instance, diagnostic ST elevation in the absence of left ventricular (LV) hypertrophy or left bundle-branch block (LBBB) is defined by the European Society of Cardiology/ACCF/AHA/World Heart Federation Task Force for the Universal Definition of Myocardial Infarction as new ST elevation at the J point of an ECG reading in at least 2 contiguous leads of ≥2 mm (0.2 mV) in men or ≥1.5 mm (0.15 mV) in women in leads V2-V3 and/or of ≥1 mm (0.1 mV) in other contiguous chest leads or the limb leads. If such a condition is identified by electronics module 12 or the software installed on mobile device 24, AED module 10 notifies EMS, in an embodiment, thus potentially shortening the time to cardiac catheterization that is needed for treatment of the condition.

In certain embodiments, the specialized software for mobile device 24 is made available on a software application marketplace (e.g., the Apple App Store), a specific website on the Internet, or be uploaded manually. Alternatively, a software installer is stored on electronics module 12 such that, when a mobile device 24 is connected, the specialized software is automatically downloaded and installed on mobile device 24. In certain embodiments, the original equipment manufacturer will preload the specialized software is preloaded on electronics module 12. In certain embodiments, the battery in mobile device 24 can be used to provide power AED module 10.

Figure 2:
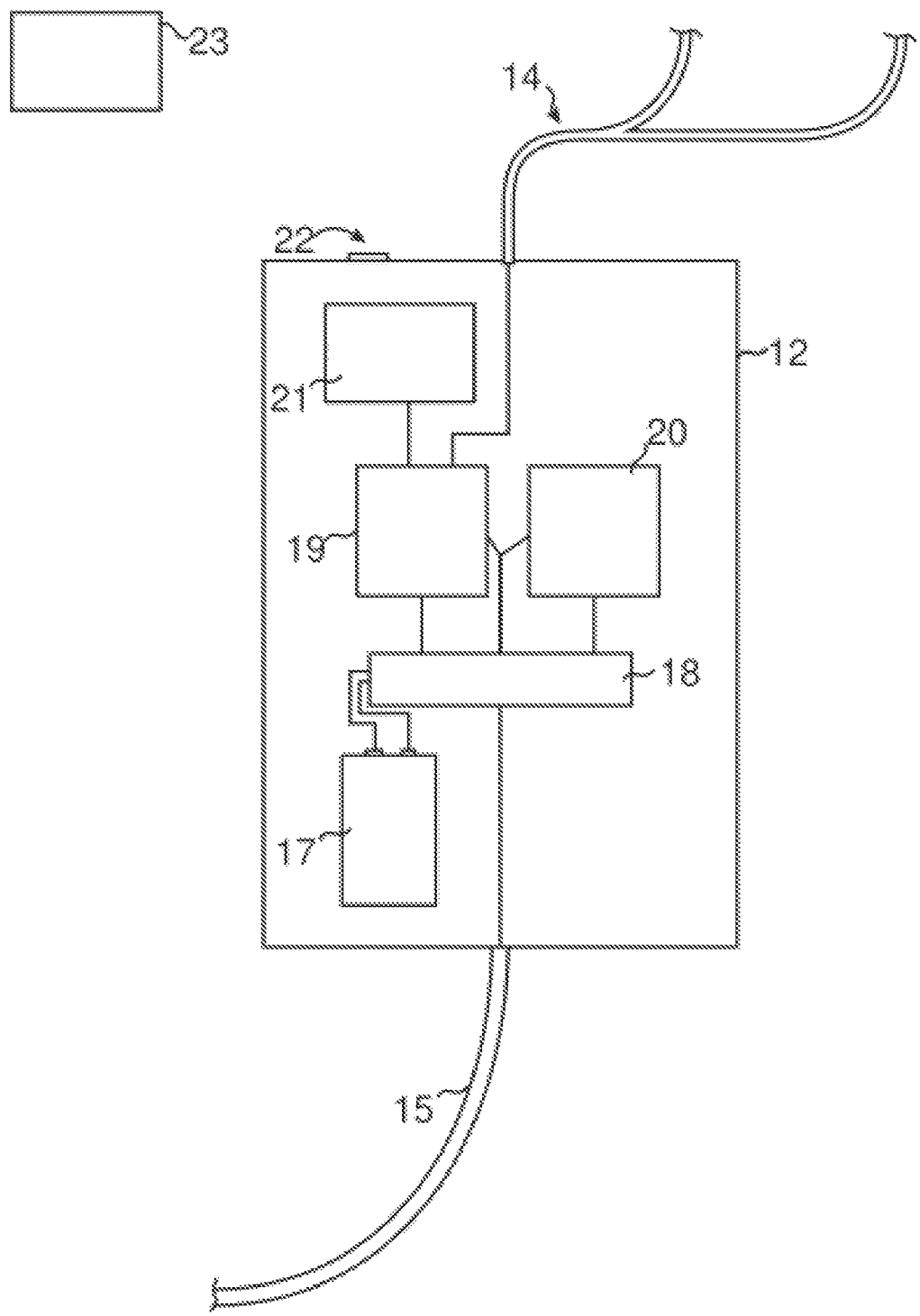
FIG. 2. Internal configuration of a control panel within an AED module, in accordance with an embodiment.

Referring to FIG. 2, certain embodiments of the internal configuration of an AED module or an electronics module 12 is shown. In certain embodiments, a battery 17 is a 9-volt battery and, in certain embodiments, can include another off-the-shelf, household battery including, but not limited to, NiMH, NiCd, lithium ion, alkaline, silver-oxide, or silver zinc batteries, singularly or in a combination thereof.

In certain embodiments, electronics module 12 also includes a series of capacitors 18 to generate and store a charge for at least one electrical defibrillation. In certain embodiments, electronics module 12 also includes a boosting element 19 for amplifying and filtering the signal received from the cardiac pads. The signal from the cardiac pads are be received via wires 14, amplified and filtered at boosting element 19, and sent from a microprocessor 20 to the software on the mobile device to be analyzed. Filtering at boosting element 19 reduces electromyography (EMG) noise and/or electromagnetic interference (EMI) in the received signal. In an embodiment, boosting element 19 allows analysis of the cardiac rhythm while active chest compression (i.e., CPR) is being administered on the SCA patient. In certain embodiments, microprocessor 20 stores downloaded software from the manufacturer to be uploaded to mobile device 24, in the event the software is not already installed on the device.

Electronics module 12 also receives from and transmits to mobile device 24 any information via wireless arrangements, such as Bluetooth and Wi-Fi using a transmitter 21. In certain embodiments, a port 22 is provided on electronics module 12 to accept additional electrodes, such as vital sign devices 23 including, but not limited to, capnography, blood pressure, pulse oximetry, and glucose monitors, smart watches, and Google Glass. Software applications equivalent to vital sign devices 23 could also be installed on electronics module 12 or mobile device 24 using wireless connections, such as Bluetooth, Wi-Fi, or audio, or a wired connection.

Figure 3:
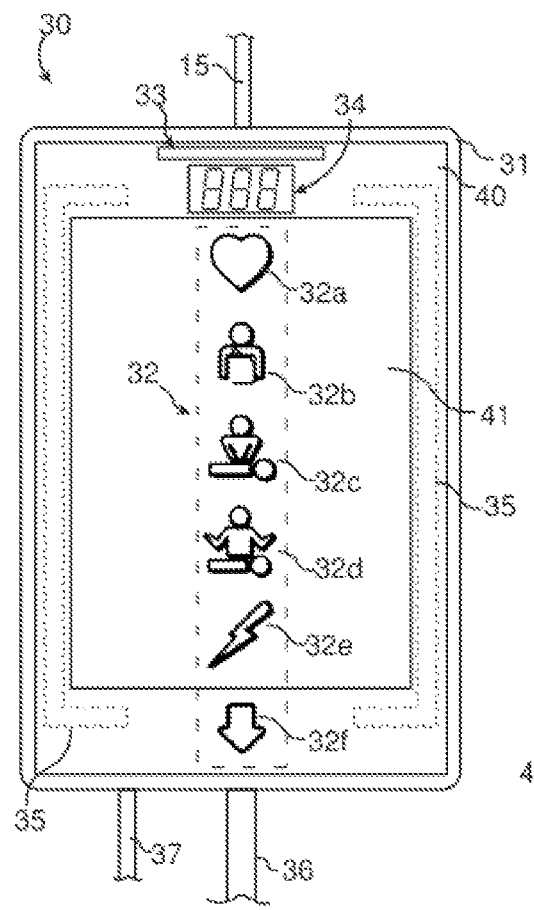
FIG. 3. Configuration of the internal components of an AED control module in certain embodiments.

In certain embodiments, a portable AED module 30 as shown in FIG. 3 is connected to mobile device 24 via wire 15. Components of AED module 30 are placed in or on a housing 31. Certain embodiments include a plurality of indicators 32 that visually show a user the steps for resuscitating a person affected with a cardiac episode. Still referring to FIG. 3, in one example, the indicators include, for example, a Heart Analysis indicator 32a, a Place AED/CPR Pad indicator 32b, a Perform CPR indicator 32c, a Clear indicator 32d, a Warning Shock indicator 32e, and a Remove Pads indicator 32f. Indicators 32 are mounted on an upper cover 41, in an embodiment. It will be appreciated by those skilled in the art that the indicators found on an AED module is not limited to these indicator types, and may include greater than or fewer than these indicator types.

Figure 4:
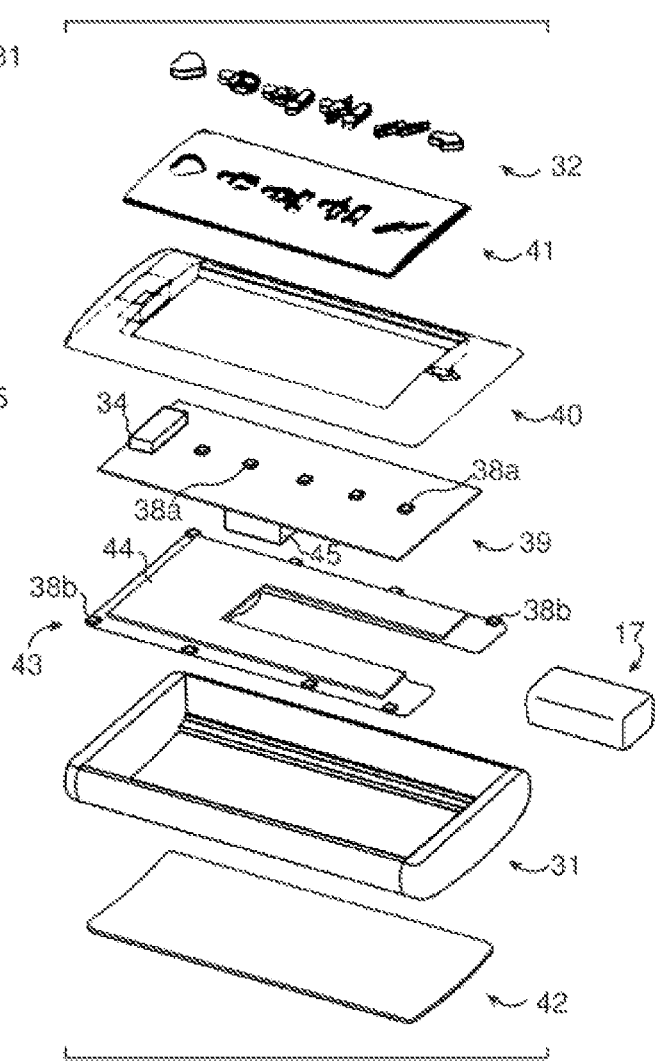
FIG. 4. An exploded view of an AED module in certain embodiments.

In certain embodiments, indicators 32 are illuminated to allow a user to visually verify the steps for performing defibrillation/CPR on a SCA patient. For example, indicators 32 are translucent, and illuminated by lights 38a found on an indicator board 39, as shown in FIG. 4. In certain embodiments, a display 34 provides further information. For example, a display 34 may be an LCD, VFD, OLED, analog, or other display to provide information. In certain embodiments, display 34 provides user feedback, status information, or other information relevant to the process of defibrillation or CPR. In certain embodiments, display 34 provides heart rate information. In certain embodiments, display 34 forms a part of indicator board 39.

Again referring to FIG. 3, in certain embodiments, an interface 33 includes speakers that transmit audio cues for using the AED and/or administering CPR. In certain embodiments, a user listens to the audio cues from interface 33 and follows the instructions of the audio cues. The speakers can transmit other information including, but not limited to, GPS location, real-time conversation with EMS personnel, instructions for use, among others. In certain embodiments, interface 33 further includes a battery life indicator.

Still referring to FIGS. 3 and 4, certain embodiments of portable AED module 30 includes a housing bezel 40. Housing bezel 40 is translucent as to allow light from lights 38b to pass through. Lights 38b are mounted on an AED power board 43 and illuminate an area 35 through housing bezel 40 to provide further visual information to assist a user while in the process of performing defibrillation and/or CPR. Illumination can occur outside of area 35 as well. It will be appreciated that lights 38a and 38b can be one or more colors as to provide color-specific information provided by any number of light sources, such as light emitting diodes (LEDs), incandescent lighting, or fluorescent lighting.

Referring to FIG. 4, in certain embodiments, a AED power board 43 includes a bulk charge storage array 44 as to hold an electrical charge. In certain embodiments, battery 17 connected with AED power board 43 provides AED module 30 the charge necessary for defibrillation. Alternatively, other power sources, such as the battery within mobile device 24 can be used. In certain embodiments, an insulation 45 provides isolation of circuitry between indicator board 39 and AED power board 43. Additionally, a back cover 42 encloses a portion of housing 31. In certain embodiments, back cover 42 may be removable as to allow a user to replace battery 17.

Figure 5:
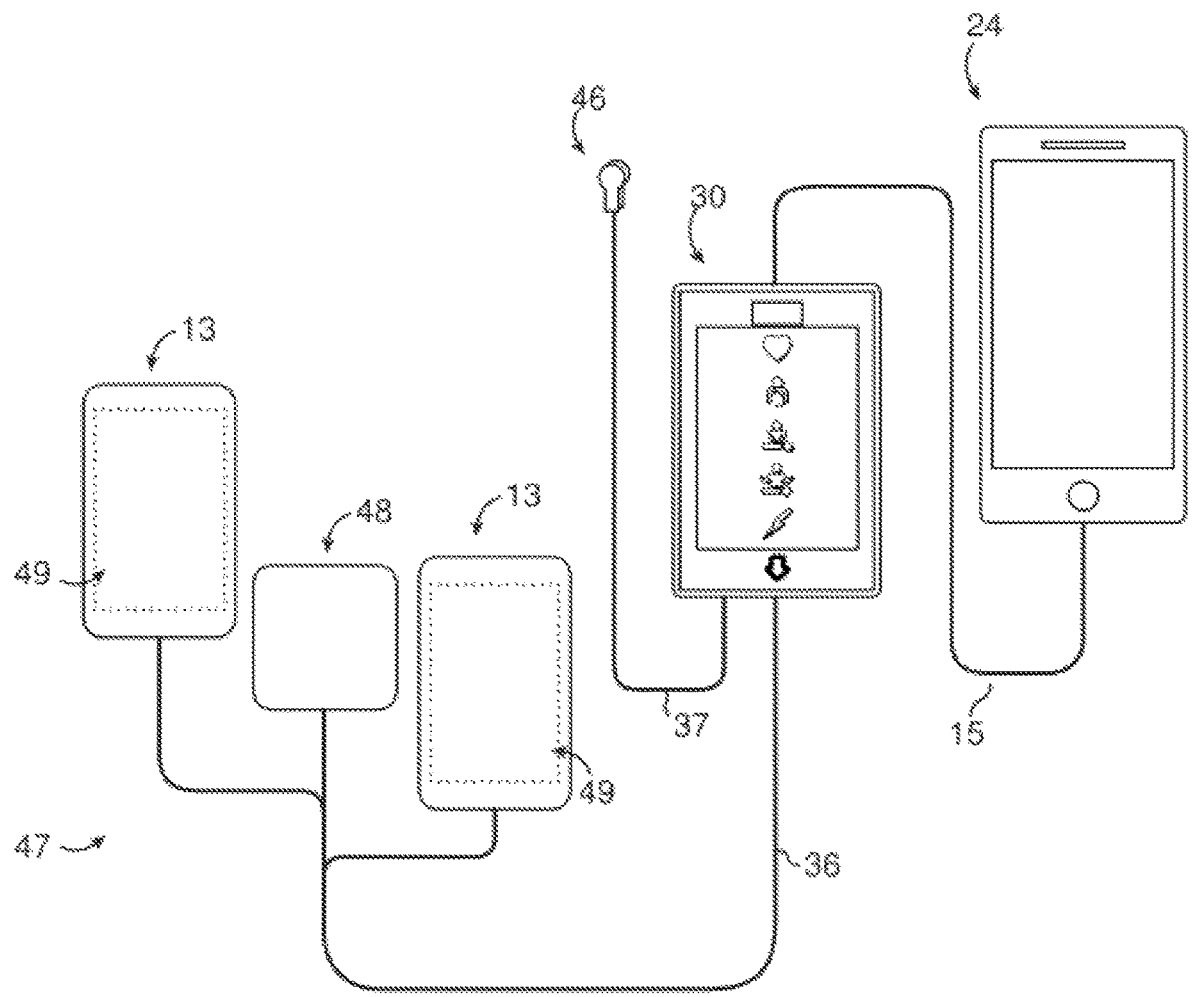
FIG. 5. Configuration of an AED module with control panel connected to a photo-plethysmography (PPG) monitor, cardiac pads, and a smartphone/mobile device in certain embodiments.

Referring to FIGS. 3 and 5, certain embodiments of AED module 30 is further connected to other components. For example, AED module 30 is connectable via wires 15, 36, 37 to a mobile device 24, photoplethysmography (PPG) monitor 46, and a plurality of pads 47. For example, PPG monitor 46 attaches to an earlobe or finger to detect, vital signs such as blood flow, heart rate, a viable heart rhythm, and blood oxygen saturation ($O_2$%). In certain embodiments, PPG monitor 46 detecting no pulse triggers AED module 30 to direct the user to start administration of CPR.

Figure 6A:
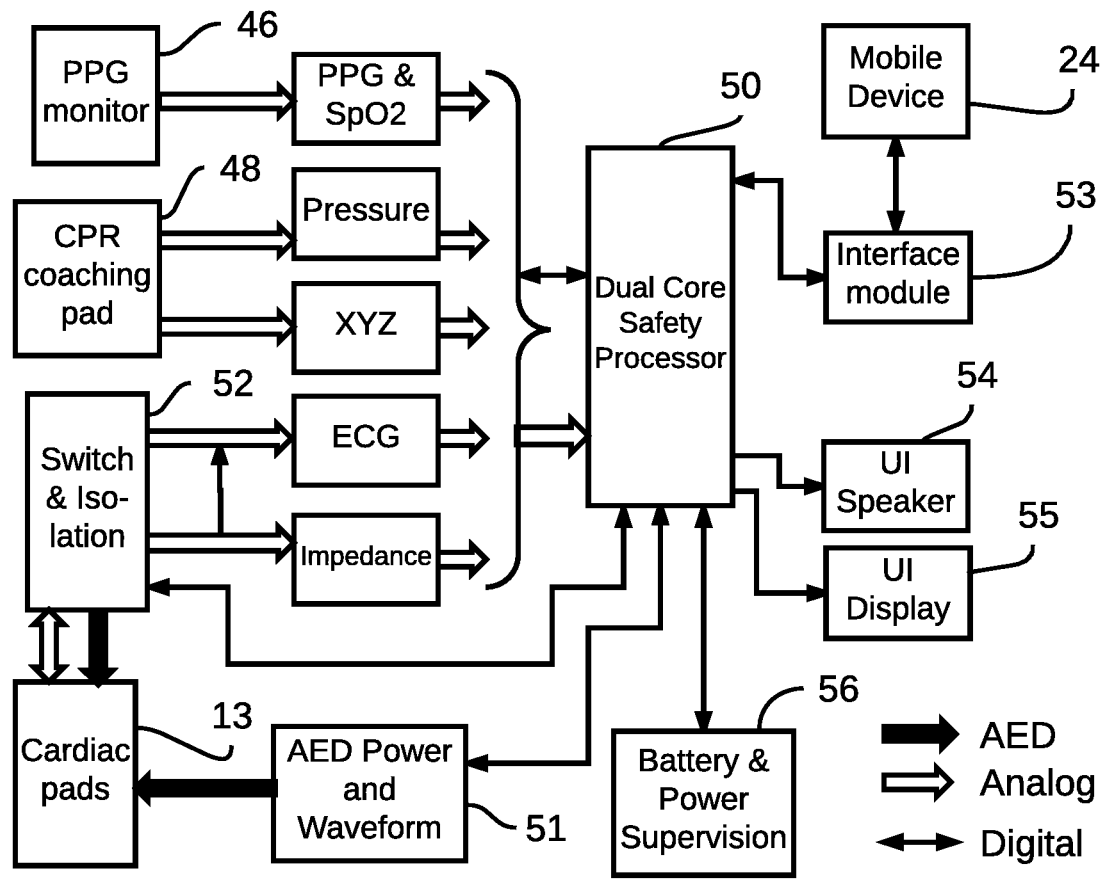
FIG. 6A. Electronic configuration of an AED module in certain embodiments.
Figure 6B:
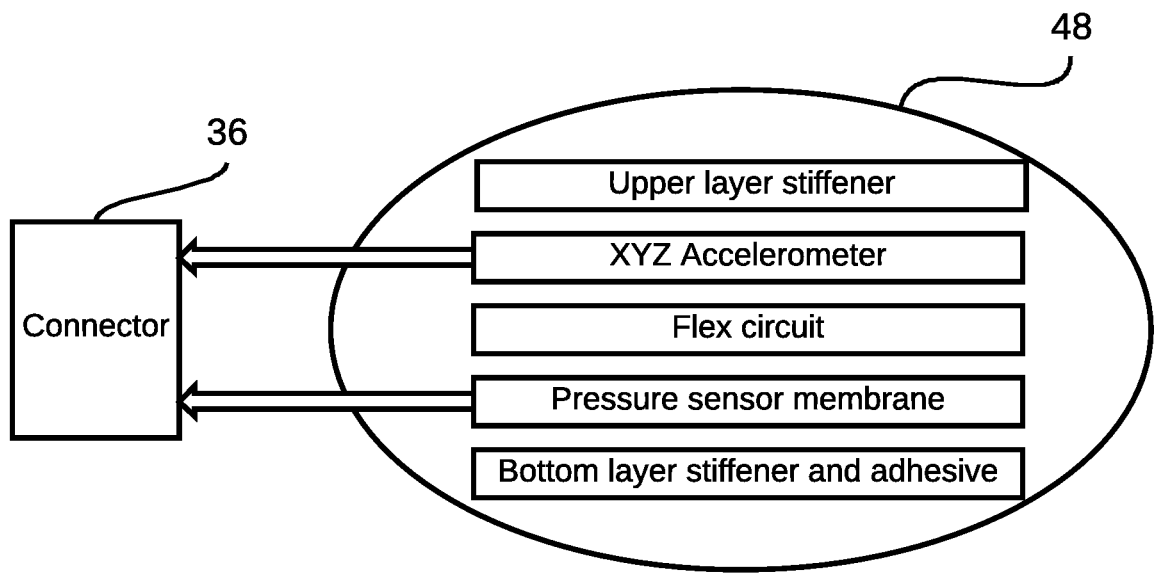
FIG. 6B. Configuration of a PPG monitor in certain embodiments.

Pads 47 include, for example, a CPR coaching pad 48 in addition to cardiac pads 13. In certain embodiments, CPR coaching pad 48 includes or is connected with sensors such as accelerometer, pressure sensor, impedance sensor, and optionally to outputs such as speakers, light indicators, and others, as shown in FIG. 6A. An accelerometer measures the movement of the pad, and a pressure sensor measures the active force and release of CPR compressions. Thus, CPR coaching pad 48 directs the user on proper administration of CPR on the patients, including directives to go faster, harder, or to stop compressions. An example of CPR coaching pad 48 is shown in FIG. 6B. Sensors in CPR coaching pad 48 receives CPR data as a user is performing CPR, and generates real-time feedback to adjust the CPR accordingly so that industry standard timing of CPR and delivery of shock are performed.

Certain embodiments of cardiac pads 13 include sensors therein to detect data from the SCA patient such as, but not limited to, body impedance and ECG signals. In certain embodiments, each of cardiac pads 13 include an area 49 that visually/graphically indicates correct placement of such pad on the patient's body.

Continuing to refer to FIG. 6A and FIG. 6B, fat black arrows indicate AED output to cardiac pads 13, fat open arrows indicate analog data transfer, and solid arrows indicate digital data transfer. Data from PPG monitor 46, CPR coaching pad 48, and cardiac pads 13 are gathered and processed by a safety processor 50. Once a determination is made that defibrillation is appropriate in a given situation, safety processor 50 communicates with an AED power and waveform module 51 and a switch and isolation module 52 to initiate and deliver an electric shock to cardiac pads 13.

In certain embodiments, safety processor 50 communicates with mobile device 24 through an interface module 53, such as a lightning or USB connector. Information regarding the patient status, defibrillation instructions, CPR instructions, emergency services communication, and others described herein are communicated from the safety processor 50 to the interface modules 53 using visual and audio cues, such as via a user interface (UI) speaker 54 and a UI display 55. Safety processor also communicates with a battery and power supervision module 56.

In certain embodiments, portable AED module 30 can be used as a stand-alone device, without connection to a mobile device. When used alone, AED module 30 provides, for example, three electric shocks with a biphasic waveform, each shock with a charge level suitable for therapeutic use and a delivery time of 1 minute or better at an ambient temperature of 0° C. from one standard household battery or battery pack, such as a 9V battery. For instance, AED module 30 starts to charge as soon as AED module 30 is powered on. In certain embodiments, delivery of the shock occurs within 1 minute of starting the charging sequence, after detection of an appropriate shockable cardiac rhythm. LED icons or indicators 32 located on AED module 30 prompts the user visually and with audible prompts to guide the user through the appropriate steps of setting up AED module 30 for defibrillation, according to industry-recommended standards. In some cases, AED module 30 directs the user to initiate CPR, if no pulse is detected from a PPG monitor, which can be provided as part of AED module 30, and if no pulse confirmed by the user. In such a case, certain embodiments of AED module 30 provide real time CPR guidance with feedback, as previously discussed. In certain embodiments, pressure sensors in AED coaching pad 48 monitor patient chest recoil during CPR administration. In certain embodiments, AED module 30 coaches the user through the proper rate and depth of CPR using an impedance sensor and accelerometer. For instance, an XYZ accelerometer, used to measure acceleration and movement of AED coaching pad 48, and a pressure sensor membrane, used to measure active force and release of each CPR compression, send CPR-related data to AED module 30 via a connector (such as wire 36) to provide user feedback regarding the effectiveness of the CPR efforts, in accordance with an embodiment. AED coaching pad 48 includes, for example, an upper layer stiffener, accelerometer, flex circuit, pressure sensor membrane, and bottom layer stiffener with adhesive, in the embodiment shown in FIG. 6B. In certain embodiments, the guidance provided in the use of AED module 30 adheres to guidelines set forth by industry standard organizations, such as the American Heart Association (AHA) for steps in addressing cardiac arrest.

When an AED module is used with mobile device 24, the above features, as well as additional features can be provided. In certain embodiments, AED module 30 receives geolocation data from mobile device 24. When AED module 30 is connected with mobile device 24, a software application is automatically opened. The communication capabilities of mobile device 24 can be used to contact EMS (such as "911" in the U.S.) and provide location data to a dispatcher that receives the communication. In an embodiment, a Short Message Service (SMS) message is sent to EMS on current status of the SCA patient, and continue to update EMS of any changes to the SCA patient's condition. Information delivered to EMS includes, but not limited to, details of any shock provided, return of spontaneous circulation (ROSC), current heart rate, pulse oximeter readings, and cardiac rhythm status. Providing this information will give EMS or the hospital the ability to better prepare for needed intervention in care of the specific SCA patient.

Figure 7:
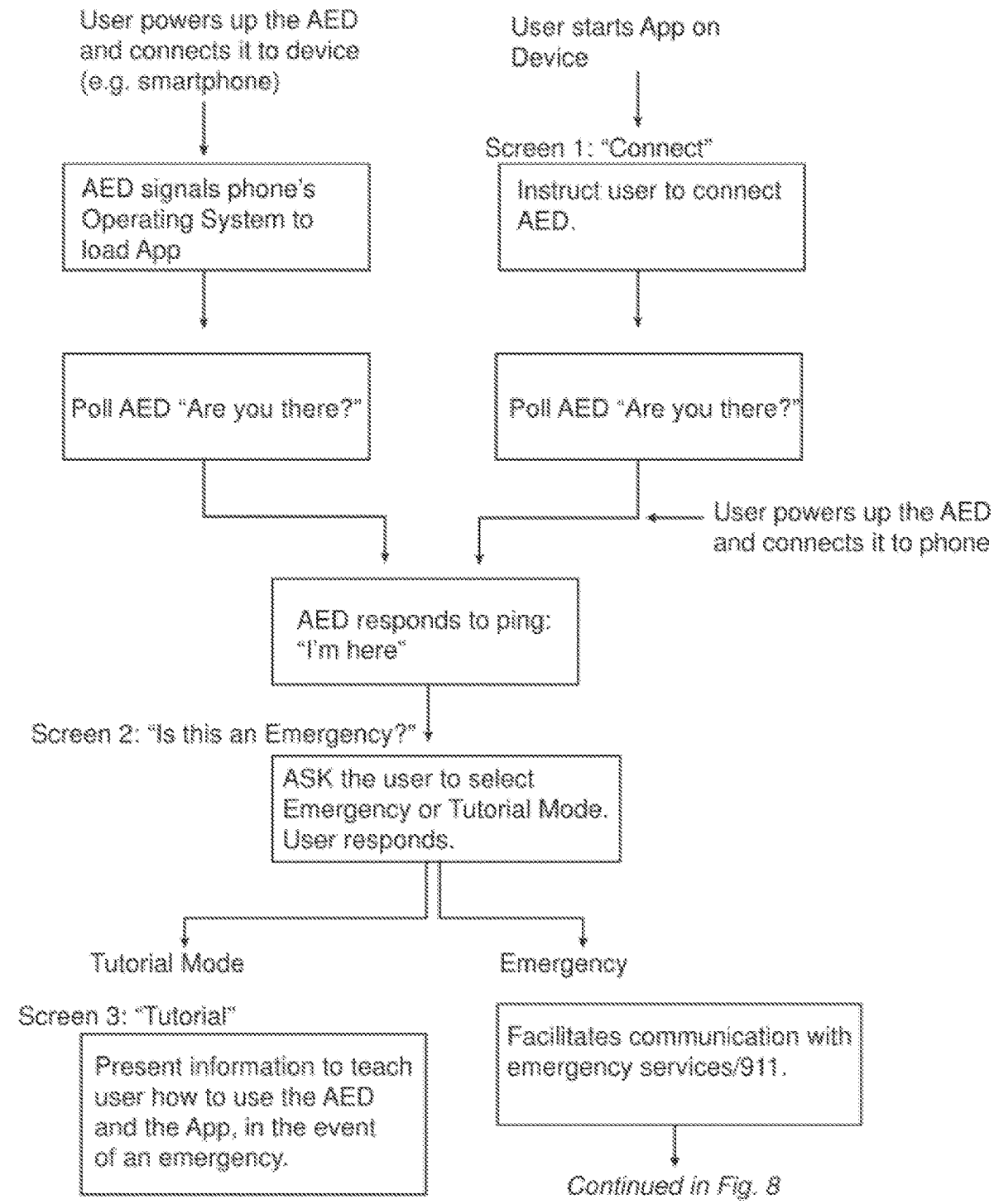
FIG. 7. Flowchart showing interaction of the user with embodiments of an application, control module, smartphone, and emergency services.
Figure 8:
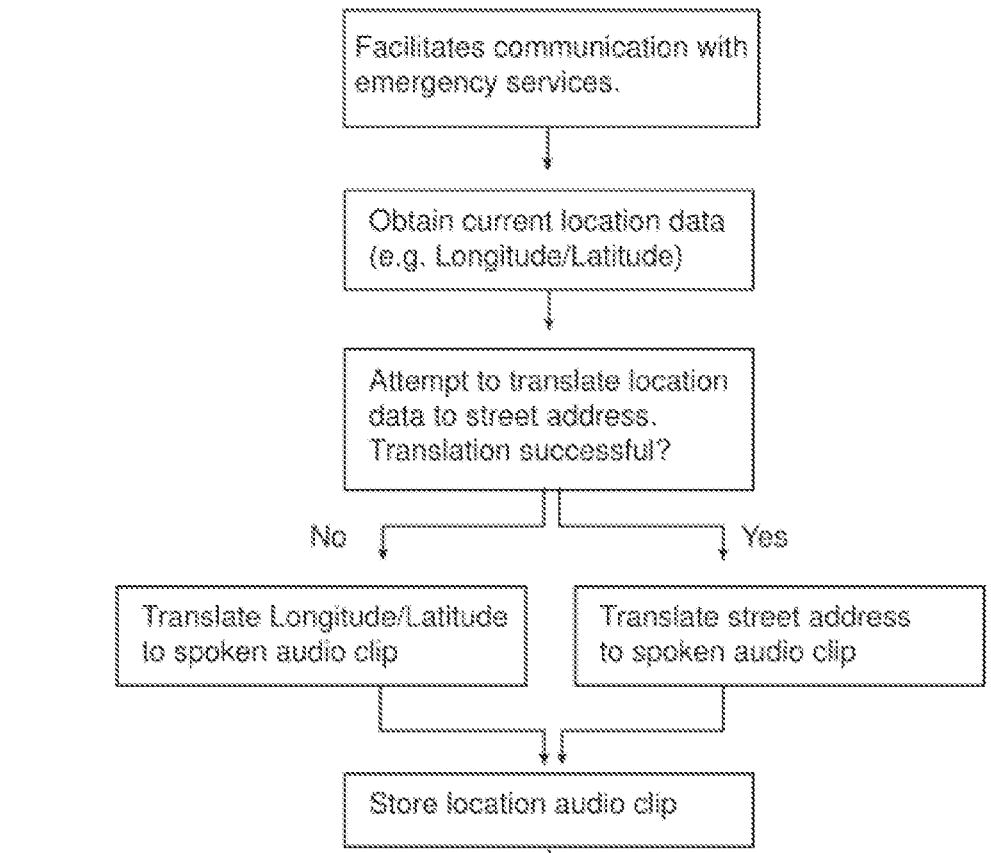
FIG. 8. Flowchart showing interaction of the user with embodiments of an application, control module, smartphone, and emergency services.
Figure 8:
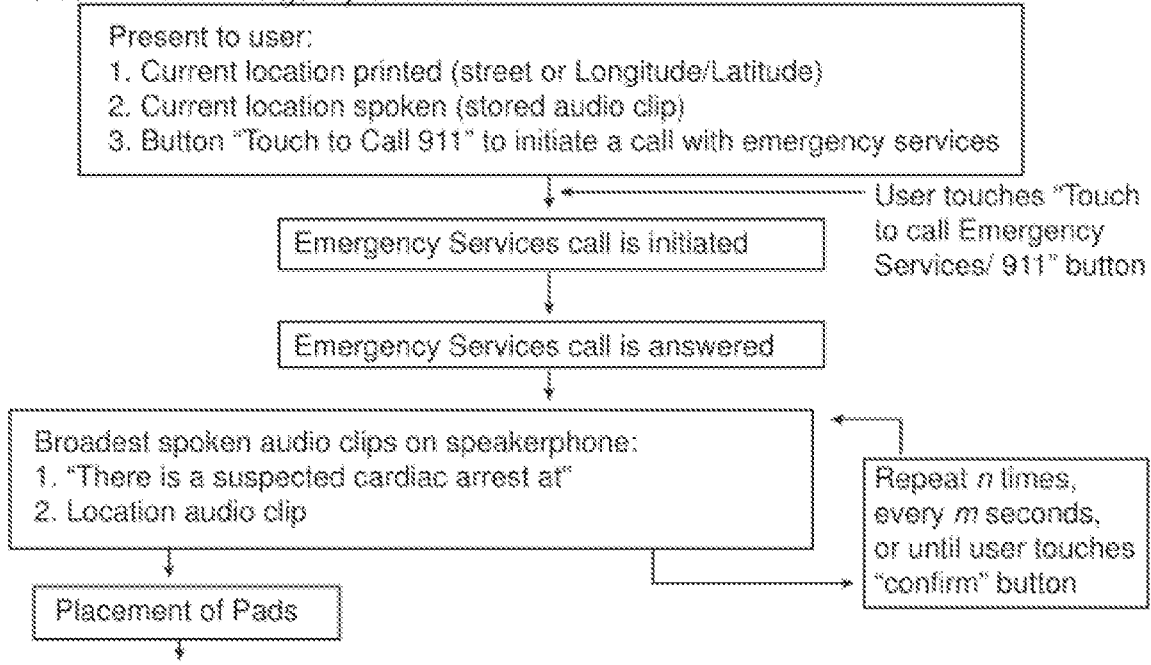
Figure 9:
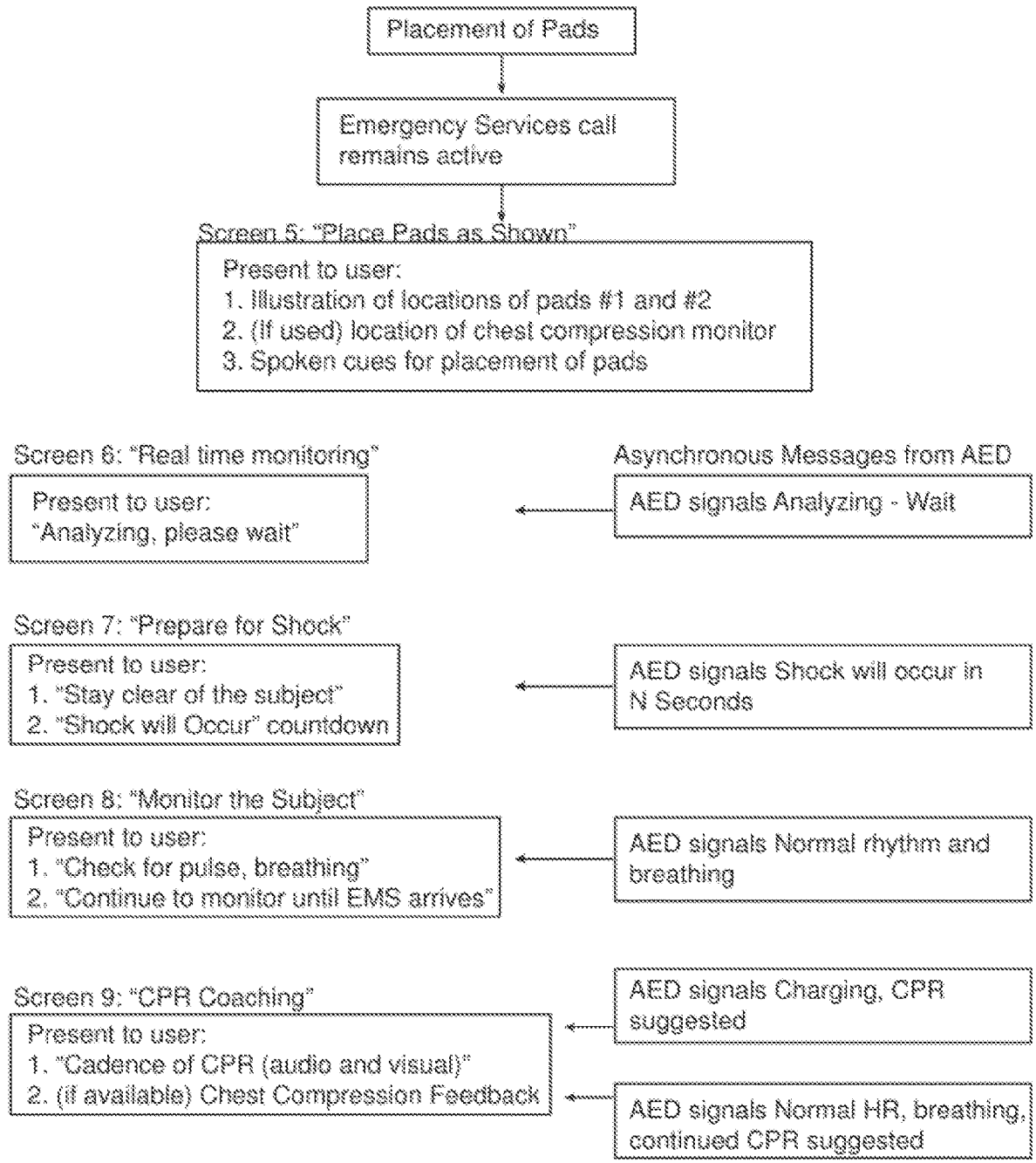
FIG. 9. Flowchart showing interaction of the user with embodiments of an application, control module, smartphone, and emergency services.

FIGS. 7-9 show the steps involved in using a portable AED module, in accordance with an embodiment. Certain embodiments include initiating an application; the application asking if there is an emergency situation; requesting to call emergency services; providing location to EMS via an automated voice over the device and via text message; automatically placing the open call to the emergency services on speakerphone; placing a PPG monitor; suggesting that CPR should begin if no pulse is detected; checking for pulse confirmation; providing a prompt via audio and visual displays on a screen to ensure effective compression is being performed; determining a person providing CPR is fatigued; recommending to change provider if low quality CPR is being performed; notifying when analyzing rhythm while CPR is in progress; notifying a person performing CPR and EMS via the speakerphone that a shockable/non-shockable rhythm is detected; notifying that victim is able to be shocked and advising to stop CPR and not to touch the patient; resuming CPR; recommending checking for pulse and responsiveness if PPG monitor detects a pulse and if a viable rhythm is detected; placing the patient in a recovery position displayed on the screen; and continuing to monitor the patient. In certain embodiments, an AED module includes other components, including but not limited to a GPS tracker, mobile phone services, modem, and Wi-Fi to communicate with emergency services.

Figure 10:
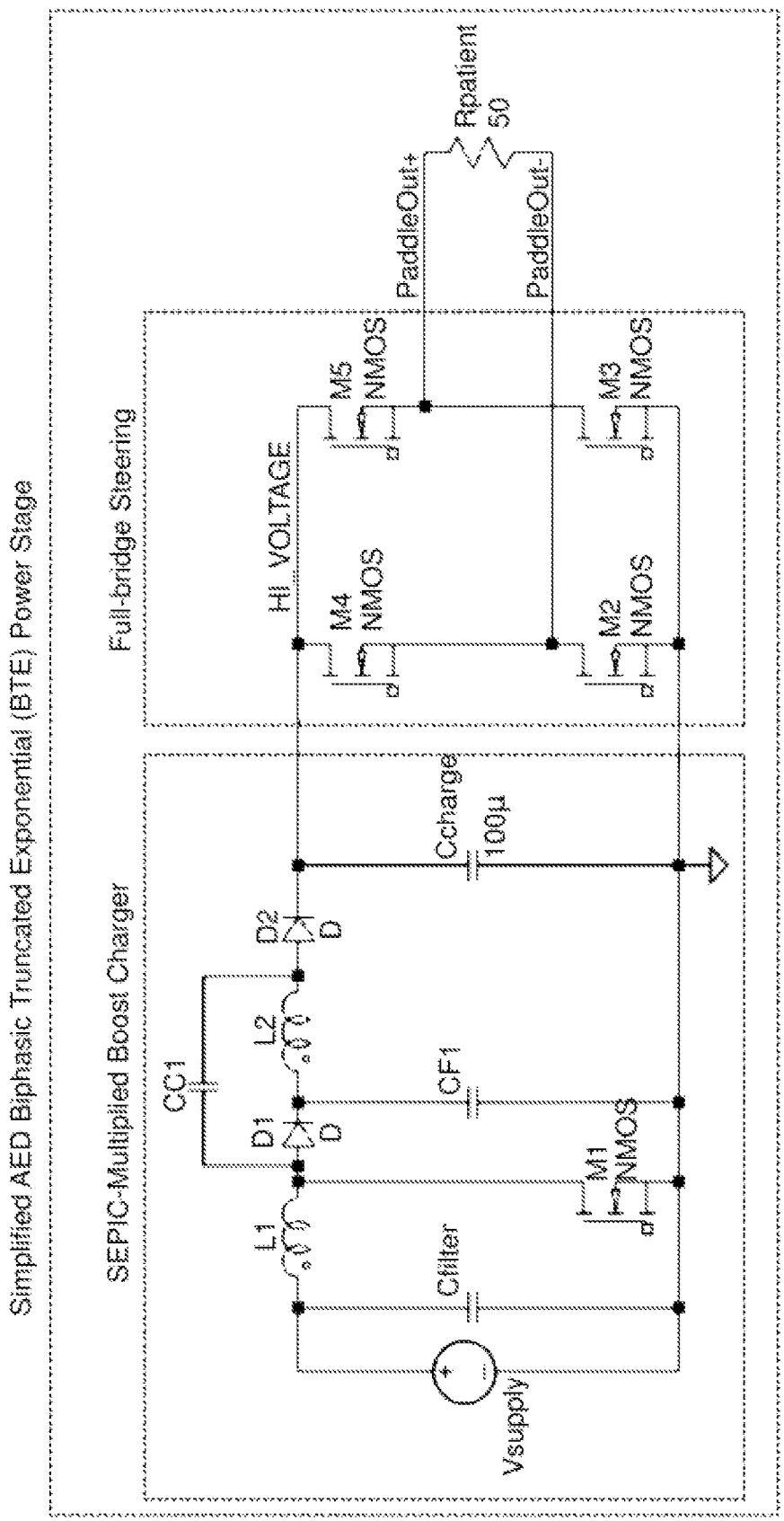
FIG. 10. A simplified AED Biphasic Truncated Exponential (BTE) power stage in certain embodiments.

Referring to FIG. 10, an exemplary circuitry for generating a charge for defibrillation. In certain embodiments, a simplified AED Biphasic Truncated Exponential (BTE) power stage is an energy-based, two stage design having a constant current boost charger (e.g., a SEPIC multiplied boost charger) supplying a bulk energy storage capacitor, followed by a high voltage full-bridge for steering the positive- and negative-half phases. FIG. 12 shows an alternative embodiments of an alternative AED module, which includes a tapped inductor boost charger along with full-bridge steering. In an example, high-voltage and current-sensing feedback are provided to the microprocessor to prevent incorrect dosing and detect error conditions. Low-voltage ECG sensing stages are isolated by relays to prevent overvoltage damage during shock delivery. The current charger uses a low current constant charge rate (in the milliamp range) controlled by pulse-width modulation (PWM) signals from the microprocessor to charge the energy storage capacitor to the prescribed amount of energy within 60 seconds or less. In an example embodiment, a charge time of approximately 45 seconds or less has been achieved using four CR123 batteries as the power source. This length of time and level of charging current is such that a standard 9V alkaline battery can be used to meet the goal operating time of several hours with at least 6 fully rated shocks at full battery conditions and three shocks and 15 minutes of operating time at minimum indicated battery level prior to AED use. The output current is steered through the positive and negative phases using, for instance, a high-voltage full-bridge performing hard switching of the 10-20 ms total duration pulses. The phase transitions times are determined based on the body impedance (from 50 ohms to 150 ohms), as seen for example in FIG. 11. That is, by adjusting the timing and amplitude of the positive and negative phases, the total energy of the shock applied to the SCA patient can be modified for the specific patient. In an exemplary embodiment, the body impedance is measured using the existing wiring of the cardiac pads by sending a low voltage square wave across the cardiac pads and calculating the load between the cardiac pads detected when the polarity of the square wave is reversed.

Figure 11:
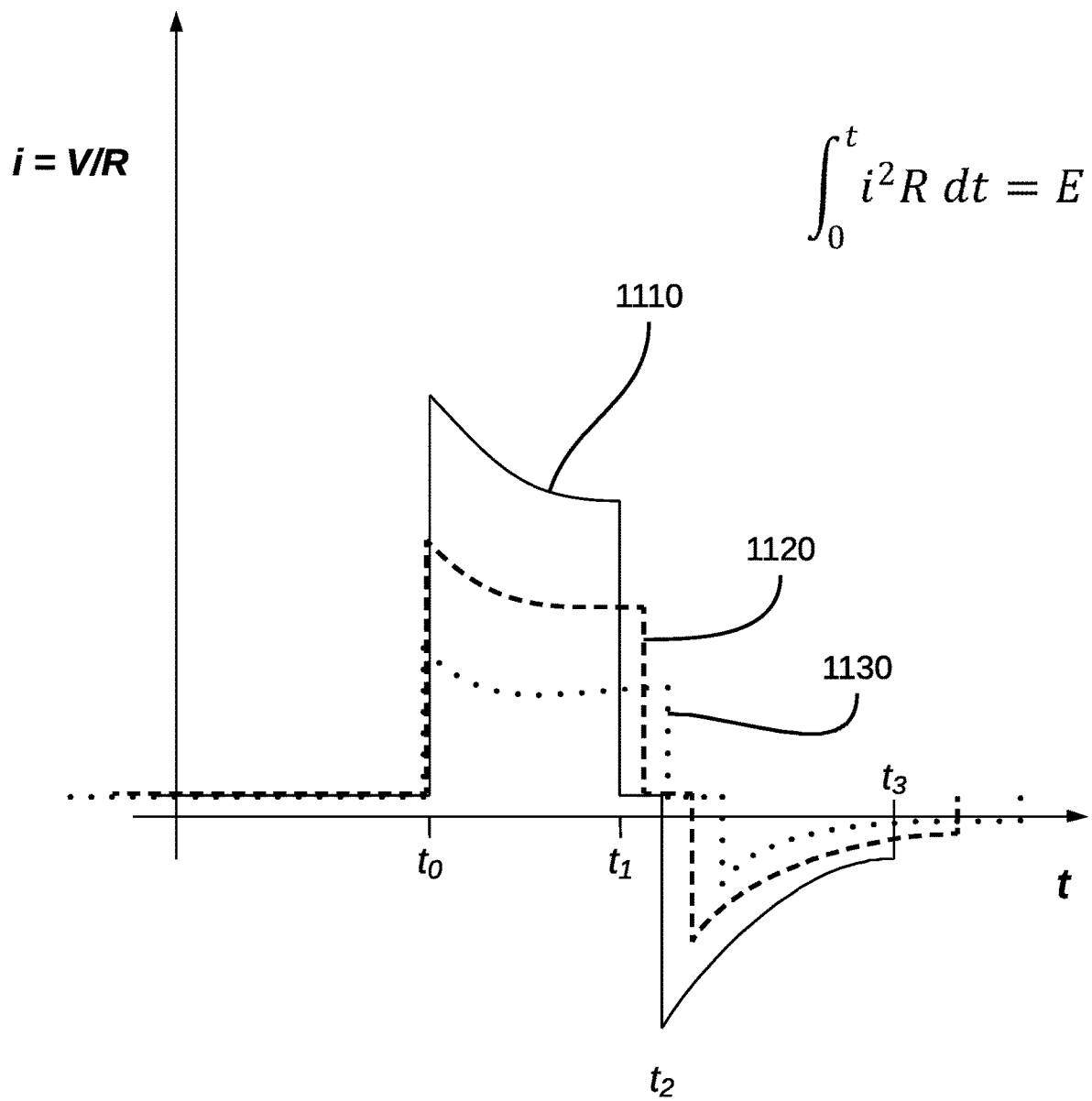
FIG. 11. A graph showing adjustments made to the shock waveform based on body impedance, in accordance with an embodiment.
Figure 12:
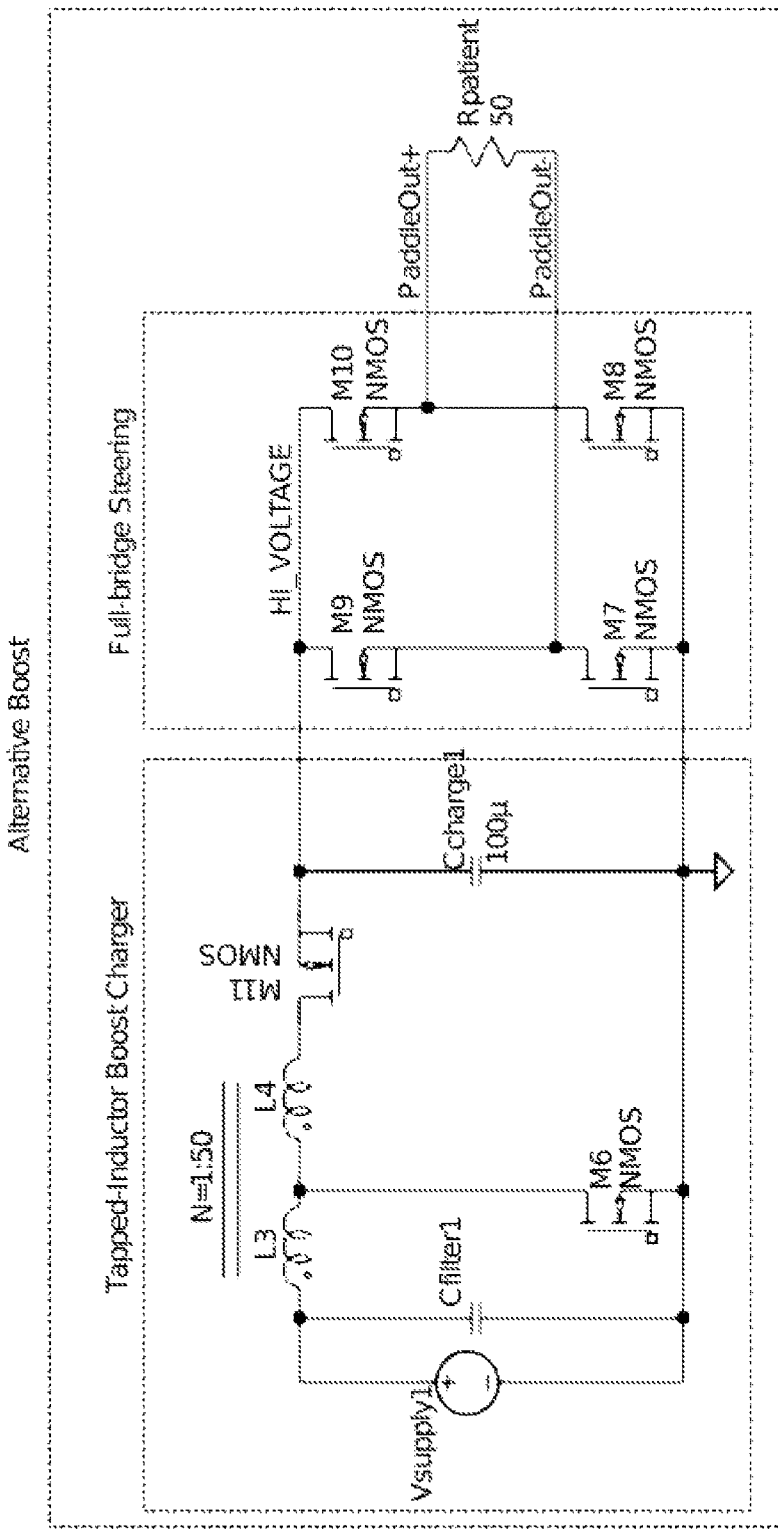
FIG. 12. An alternative boost power stage in certain embodiments.

In the example shown in FIG. 11, the waveforms correspond to different transition times and amplitudes calculated for different body impedance values, in accordance with an embodiment. The total energy applied to the SCA patient per shock can be calculated using the following Eq. 1:

$$E = \int_0^t i^2 R \, dt \qquad \text{[Eq. 1]}$$

where $$i = \frac{V}{R} = \text{current,}$$

R=body impedance, and t=time. In FIG. 11, a waveform 1110 corresponds to R=50 ohms, a waveform 1120 corresponds to R=75 ohms, and a waveform 1130 corresponds to R=125 ohms. For instance, as shown, an energy peak of 200 J for body impedance of 50 ohms corresponds to a current of i=~40 Amps. For the example of a charge provided by a 120 microfarad capacitor holding a charge of 1640V, the switching and end times ($t_2$ and $t_3$ in FIG. 11) are summarized in TABLE 1.

TABLE 1

| Body impedance (ohms) | Switch time $t_2$ (milliseconds) | End time $t_3$ (milliseconds) |
|---|---|---|
| 25 | 1.38 | 4 |
| 50 | 2.76 | 8 |
| 75 | 4.13 | 12 |
| 150 | 8.27 | 24 |
| 200 | 11.02 | 32 |

It is important to note that the embodiments described herein require innovative solutions to problems not faced by previously available AEDs For instance, the embodiments described herein provide:

1. A highly portable AED with a form factor that is much smaller (e.g., the circuit boards fit within 6-inches by 6-inches by 2-inches in certain embodiments) than that of the commercially-available AEDs;
2. Circuitry for generating industry-standard biphasic shock from consumer batteries that are readily available to ordinary users;
3. The AED being ready to deliver the generated charge to the patient within the FDA-required time frame; and
4. Optionally, the ability for the AED to connect with a mobile device for communication with emergency medical services personnel.

These are requirements that go beyond those that have been faced by previous AED manufacturers.

It is particularly emphasized that, in order to achieve the necessary performance from a compact, portable AED from a household battery, the coordination of the electronic design and firmware is important. It is particularly emphasized that the generation of shock, and the regulation thereof, powered by a commercially-available household battery and presented in a user-friendly, compact package at an affordable price point is a significant engineering achievement. There are considerable challenges in reducing the package size of the AED, especially with the various voltage converters and high voltage drivers involved in generating the therapeutic shock according to best practices from a household battery. In particular, considerable engineering ingenuity is required to achieve the necessary performance under the above listed limitations, particularly as the operation of the high voltage device by an untrained user involves extensive consideration of safety measures provided in the physical features as well as the logic involved in the firmware and ease of use in the user interface. No device equivalent to the embodiments described herein is currently known.

The generation of the biphasic waveform from common household batteries, such as one or more 9V or CR123 batteries, is a significant challenge due to the limited voltage and current provided by such batteries. The circuitry required to generate an adjustable biphasic waveform, such as those illustrated in FIG. 11, from household batteries while fitting within a highly portable package is a unique challenge solved in the embodiments described herein.

For instance, focusing on the H Bridge shown as "Full-bridge Steering" in FIG. 10, the method used to generate the biphasic waveform in certain embodiments described herein is different from existing designs, such as those that separately generate the positive and negative phases then combines them using a time delay circuit when administering to the patient. In an exemplary embodiment, the biphasic waveform is generated by discharging a single high voltage capacitor using an H Bridge configuration under microprocessor control.

More specifically, in an exemplary embodiment shown in FIG. 10, switches M4 and M3 are closed, then opened. Subsequently, switches M5 and M2 are closed, then opened. Software is used to determine the appropriate timing of each phase to deliver a total charge of, for instance, 150 J in accordance with Eq. 1 above, with equal charge in each direction of the decaying resistor-capacitor (RC) potential for each phase (i.e., M4-M3 combination, then M5-M2 combination). This exemplary H Bridge configuration allows certain embodiments to generate the required biphasic waveform using only one charge reservoir, thus delivering all of the required charge from the one charge reservoir for both polarities. Furthermore, firmware logic is used to prevent erroneous control of the H Bridge (e.g., combinations such as M4-M2 and M5-M3 for the components shown in FIG. 10). An H Bridge board, such as IXYS H-bridge driver board, is an example of a board that can be configured as disclosed herein. Additional potential candidates for use in the H Bridge configuration are, for example, Powerex modules and Isolated Gate Bi-polar Transistors (IGBTs), Texas Instruments modules and IGBTs, Infineon PCB modules, CT-Concept/Technologie Power Integrations, IXYS drivers and IGBTs, and others suitable equivalents.

Another point of innovation for certain embodiments described herein is the DC-DC converter implementation shown, for example, in FIG. 10 and FIG. 12, capable of enabling capacitor charging within one minute, or as little as less than 30 seconds. In an example, the high voltage DC-DC converter uses a flyback transformer with a forward diode topology. Multiples of such DC-DC converters can be placed in parallel using diode ORing to reduce the charge time, with a trade-off of increasing the current draw from the battery. In an example, the power that can be generated from a 9V at 1 A is 9 W. If an energy output of 200 Joules, which is equivalent to 200 W*seconds, then this level of energy output can be obtained in 200 W*seconds/9 W=22 seconds at 100% battery efficiency. Efficiency may be less, which could increase the charge time.

Alternatively, three or four CR123 batteries, which are also readily available with nominal voltage of 3.0V each, may be used in place of the 9V battery to supply sufficient charge within the required time frame. In an exemplary embodiment, the circuit design is based upon the use of a 9V operating at a current of 1 A, which can be achieved with parallel or series combinations of batteries. For instance, parallel combinations of N 9V batteries will require diode ORing and will supply 1/N current capability for each. Series combinations will require each battery to be 1/N of 9V and to deliver the full 1 A. CR123 batteries (for example, Energizer Lithium/Manganese Dioxide EL123AP batteries (http://data.energizer.com/pdfs/123.pdf)) can deliver 3V at a continuous current of 1.5 A, and therefore three such CR123 batteries in series would meet the criteria.

In certain embodiments, a further variation for the high voltage DC-DC converter is used in order to more efficiently produce the required biphasic waveform within the FDA-required charge time. This variation is based on the knowledge that lower voltage DC-DC converters can produce higher current output than higher voltage DC-DC converters because converters are usually designed to put out a fixed amount of power. While a single off-the-shelf DC-DC converter does not provide a sufficiently short charge time, a multi-tier approach can be used by diode ORing the output of multiple DC-DC converters with different voltage capacities.

For example, different variants of off-the-shelf DC-DC converters can be tiered to yield outputs stepped from 2000V to 4000V from a 12V input. If a 9V input is connected to the same configuration, outputs would step from 1500V to 3000V.

This diode ORing concept for faster charging utilizes the lower voltage converter to deliver higher charging current up to 1500V, and then one or more of the higher voltage converters to bring the voltage up to the final desired value. In other words, rather than using a single, or even two, high voltage DC-DC converter, faster charging can be achieved by using a combination of lower voltage and higher voltage DC-DC converters in a tiered configuration. A combination of high voltage DC-DC converters, such as EMCO HV DC-DC converters American Power Designs, and LinearTech DC-DC converters with custom transformer and circuit topologies, can be used to implement the embodiments as disclosed herein.

In certain embodiments, the firmware merges control logic for the circuitry, as well as impedance measurement across the cardiac pads (i.e., the impedance related to the patient's size) in order to adjust the parameters of the applied biphasic waveform to the specific patient. As an example, the microcontroller unit (MCU) within the AED serves to provide overall control of the performance of the AED in a variety of ways.

In an embodiment, the MCU has several responsibilities in the fully functional AED. For instance, the MCU:

1. Delivers a shock as a biphasic waveform with a precise shape, according to precise timing specifications.

2. Monitors an ECG signal, sensed from the cardiac pads, and to differentiate between "shockable" rhythms and "unshockable" patterns. The associated algorithm runs internally within the AED without real-time access to the cloud, or to any attached device such as a smartphone. Such an algorithm is defined, in the present disclosure, as a shock indicator algorithm (SIA). The specific conditions identified required for differentiation between shockable and unshockable cardiac rhythms by the SIA follow guidance from industry organizations, such as the recommendation of ACLS and AHA. In an embodiment, the SIA is prioritized above other processing activities within the AED such that the SIA interrupts any other activities in the MCU to commence the shock protocol, to the exclusion of other activities. Further details regarding the SIA are provided hereinafter at the appropriate juncture.

3. Guides users through the shock protocol, such as by displaying instructions to stand clear, allowing the required amount of time for rescuers to comply with those instructions, and finally triggering the shock itself.

4. Monitors physiological signals pertinent to the determination of whether to perform CPR.

5. Monitors the performance of a person administering CPR, including sensor measurements related to the CPR itself as well as physiological data from the patient, so as to provide guidance to even a lay person without CPR training.

6. Connects and communicates with a smart phone, via a wired or wireless connection, for enhanced features such as AED and CPR guidance, and communication with emergency medical services personnel.

7. Controls certain AED hardware components such as, for example, controlling a charging sequence in preparation for administering a shock.

8. Detects the attachment status of the cardiac pads to the SCA patient such that, in the case the cardiac pads are not well-attached to the SCA patient, for example, the AED alerts the user to the condition.

The activities in the above list need not happen simultaneously. For example, the device can progress through a charging sequence (item 7 above), while providing ECG signal input to the SIA (item 2 above) and also monitoring the patient for other physiological signs useful to the administration of CPR (item 4 above), as well as monitoring the user's CPR performance (item 5 above).

If the SIA indicates that a shock is needed, the MCU continues with the timed charging sequence (item 7 above), if not yet completed, while simultaneously guiding the user through the shock protocol (item 3 above) and possibly continuing to monitor physiological signs (item 4 above). In an exemplary embodiment, the MCU contains logic such that the administration of a shock is only commenced when certain criteria are fulfilled. For example, the MCU can be set such that shock is administered only when: 1) a shock sequence was initiated by the user; 2) the charging sequence has been completed; and 3) the shock protocol has been completed with no alerts, such as due to displaced cardiac pads.

As another example, during the actual administering of a shock, the MCU turns off all other AED activities not essential to that primary function to avoid conflicts and to protect sensitive components. Additionally, after a shock has been administered, the MCU resets some of those other activities to a new-start state, as data gathered prior to the shock may be no longer relevant or accurate.

In an exemplary embodiment, the MCU has several tasks related to the shocking function, including:

1. Monitoring vital signs of the SCA patient and engaging the SIA to look for a shockable pattern;

2. Guiding the user through the shocking protocol;

3. Managing the charging sequence; and

4. Controlling the shock waveform produced by the AED circuitry.

More specifically, in an embodiment, the MCU provides guidance to the user, such as to "stand back" or "stay clear" in anticipation of the shock administration, including a protocol to allow the user sufficient time to comply before administering the shock. The MCU can also provide logic to combine information about, for example, the placement of the cardiac pads on the SCA patient, the readiness state of the hardware (e.g., capacitor charged), and the analysis by the SIA and, if all of the requirements are satisfied, instruct the user to stand clear and, after a reasonable time, commence the shock.

In an embodiment, the MCU manages specific timing aspects of the generation of the biphasic waveform produced by the AED. For example, the MCU manages a sequence of several carefully timed processes that, once initiated, progress through all the steps in a prescribed order, all the way to completion without interruption. In an exemplary embodiment, the state machine within the MCU firmware administers the setting of the timers of various durations, and uses these timers to drive the output pins to control the AED hardware. For instance, the state machine includes eight unique states with timing on the order of milliseconds with a timing precision of 100 microseconds.

In an example, several events are required before a shock is administered. These include:

1. A "shock needed" signal from the SIA (i.e., a shock request);

2. Completion of guidance sequence, alerting the user to stand back and away from the SCA patient; and 3. Indication from the circuitry hardware that the charging function has been completed.

These required events happen asynchronously with respect to each other. For example, the shock request can immediately trigger the user alert operation, or the charging sequence can be set to begin as soon as the AED unit is turned on, such that this step has no direct connection with the shock request from the SIA. Additionally, the MCU can include features such as, but not limited to:

1. The charging sequence completed (e.g., "HV_Ready") is a hardware interrupt, via an Interrupt Service Routine (ISR);

2. The shock request is a message from one part of the firmware to another, or from a separate hardware component, if that solution is provided onboard a processor chip or the like; and 3. The actions to alert the user (e.g., via flashing lights and/or audio alerts) are managed by a clock in the firmware.

As an example, the main loop of the firmware contains the logic to check that a shock is required, and that the protocol prior to administering the shock (e.g., the user has been alerted to "stand back," the capacitors are fully charged) has been completed, and then automatically administer the shock. The firmware main loop managers, for instance: 1) charging requests; 2) shock requests; 3) discharge request to safe state (e.g., if the shock protocol has been aborted); and 4) battery test requests. Such requests can be presented to the firmware as buttons or as terminal commands. For instance, as buttons, the requests arrive in ISRs where minimal logic is allowed (e.g., no terminal output). In an example, buttons and terminal requests behave the same way; i.e., instead of direct action, the request is registered in a state variable that the main loop will check on its next iteration. Such a configuration safely allows for feedback to developers via the terminal, while still allowing the ISRs to exit quickly if necessary.

An example process flow of a firmware controlling the AED, in accordance with an embodiment, is described in FIGS. 13-19.

Figure 13:
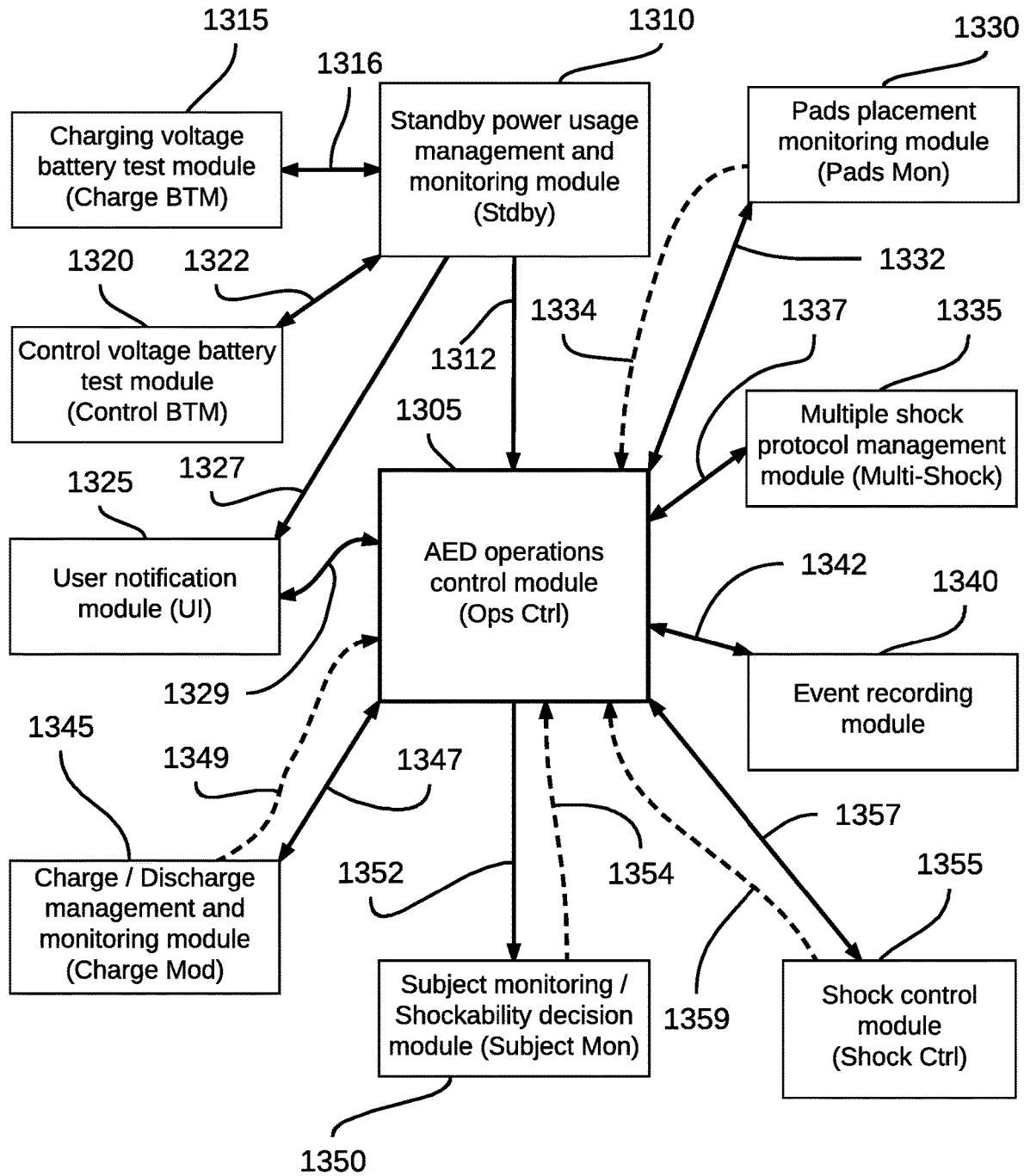
FIG. 13. A relational diagram showing the communications between an AED operations control module and other firmware within the AED module, in accordance with an embodiment.

Referring first to FIG. 13, a relational diagram shows the communications between an AED operations control module and other firmware within the AED module, in accordance with an embodiment. As shown in FIG. 13, an AED operations control module (Ops Ctrl) 1305 includes circuitry and logic to orchestrate the overall operation of the AED module, such as AED module 10 of FIG. 1. Ops Ctrl 1305 is in communications a standby power usage management and monitoring module (Stdby) 1310, which manages the operations of the AED module when in standby mode. Stdby 1310 includes circuitry and logic to maintain, for example, a microprocessor and related circuitry in a low-power mode to facilitate a longer shelf life for the battery systems within the AED module. When the user activates the AED module for treatment use, Stdby 1310 sends Ops Ctrl 1305 a signal 1312 to commence the treatment operation of the AED module.

In an embodiment, Stdby 1310 communicates with a charging voltage battery test module (Charge BTM) 1315, which includes circuitry and logic to test the battery capacity status of the battery, which powers the shock generation for the AED module. Periodically, Stdby 1310 instructs charge BTM 1315 to check the battery capacity of the main battery in the AED module, then send an indication via main battery status channel 1316 back to Stdby 1310.

In an exemplary embodiment, Stdby 1310 is also connected with a control voltage battery test module (Control BTM) 1320, which tests a control battery for powering a microprocessor and related control circuits. Periodically, Stdby 1310 instructs Control BTM 1320 via a control battery status channel 1322 to test the capacity of the control battery, then send an indication back to Stdby 1310.

Additionally, in an embodiment, Stdby 1310 communicates with a user notification module (UI) 1325, which includes circuitry and logic to manage the conveyance of information to a user regarding device maintenance, as well as during AED operation. For instance, if either a signal from main battery status channel 1316 or control battery status channel 1322 indicates that the charge of the respective battery is low and requires replacement or maintenance, Stdby 1310 sends a status alert signal 1327 to UI 1325 to display an alert indication to notify a user of the problem. UI 1325 also is in direct communications with Ops Ctrl 1305 via a UI communication channel 1329 to display user guidance or alerts during the operations of the AED module, as will be explained in detailed as the appropriate juncture below.

Continuing to refer to FIG. 13, in an exemplary embodiment, Ops Ctrl 1305 is connected with a pads placement monitoring module (Pads Mon) 1330, which includes circuitry and logic to monitor whether a user has properly attached a pair of cardiac pads onto the SCA patient. Upon initiation of the AED operations, and after Ops Ctrl 1305 prompts the user to place the cardiac pads on the SCA patient via UI communication channel 1329 to UI 1325, Ops Ctrl 1305 checks with Pads Mon 1330 via a to ensure the cardiac pads have indeed been properly attached via a pad status channel 1332. Additionally, Pads Mon 1330 can communicate with Ops Ctrl 1305 on an asynchronous basis (indicated by a dashed arrow 1334) to alert Ops Ctrl 1305 in case, for example, if a cardiac pad becomes detached from the SCA patient.

Still referring to FIG. 13, Ops Ctrl 1305 is also in communication with a multiple shock protocol management module (Multi-Shock) 1335 via a multi-shock channel 1337, in an embodiment. Multi-Shock 1335 includes logic to manage situational behavior of the AED in cases where the initial shock does not result in a return to normal sinus rhythm for the SCA patient. Ops Ctrl 1305 also communicates with an event recording module 1340 via an event recording channel 1342. In embodiment, event recording module 1340 includes circuitry and logic to manage the capture of data related to, for instance, the condition of the SCA patient, therapeutic efforts by the AED, and external communications records.

In an exemplary embodiment, Ops Ctrl 1305 manages a charge/discharge management and monitoring module (Charge Mod) 1345. Charge Mod 1345 includes circuitry and logic to manage the charging of the capacitor for storing the charge to a correct level in order to administer a therapeutic shock. Charge Mod 1345 also includes circuitry and logic to manage the discharge of the capacitor in the event that a therapeutic shock is not required, such that the AED can be handled safely and returned to storage in a safe state. Charge Mod 1345 communicates with Ops Ctrl 1305 via a charge management channel 1347 to receive and acknowledge, for example, a charge or a discharge command. Also, Charge Mod 1345 can asynchronously communicate its status to Ops Ctrl 1305 (as indicated by a dashed arrow 1349), such as to indicate the capacitor charge has been reduced to a safe handling level sometime after a discharge command has been received from Ops Ctrl 1305.

In an embodiment, Ops Ctrl 1305 also controls a subject monitoring/shockability decision module (Subject Mon) 1350, including the SIA. Subject Mon 1350 includes circuitry and logic to manage the gathering of physiological measurements, such as cardiac rhythm, body impedance, and/or ECG signal. Subject Mon 1350 also includes circuitry and logic to analyze the collected data to determine whether the SCA patient's condition is one that requires or can benefit from a defibrillating shock. Ops Ctrl 1305 issues requests to Subject Mon 1350 to determine shockability of the SCA patient via a subject monitoring channel 1352. Whenever a determination of the shockability of the SCA patient has been made, sometime after receipt of the request for shockability determination from Ops Ctrl 1305, Subject Mon 1350 send an indicator back to Ops Ctrl 1305 via an asynchronous communication (indicated by a dashed arrow 1354). Finally, Ops Ctrl 1305 also controls a shock control module (Shock Ctrl) 1355 via a shock control channel 1357. In an embodiment, Shock Ctrl 1355 includes circuitry and logic to manage the determination of the shock waveform parameters, such as the durations of the positive and negative components to a biphasic shock, based on analysis of physiological measurements such as body impedance. Shock Ctrl 1355 further includes, in an embodiment, circuitry and logic to produce a biphasic shock waveform, according to the calculated parameters, then deliver the shock to the cardiac pads placed on the SCA patient. Shock Ctrl 1355 asynchronously sends a communication to Ops Ctrl 1305 (indicated by a dashed arrow 1359) to indicate, for example, that a shock has been delivered to the cardiac pads, as well as additional information such as the waveform parameters and patient vital signs.

Figure 14:
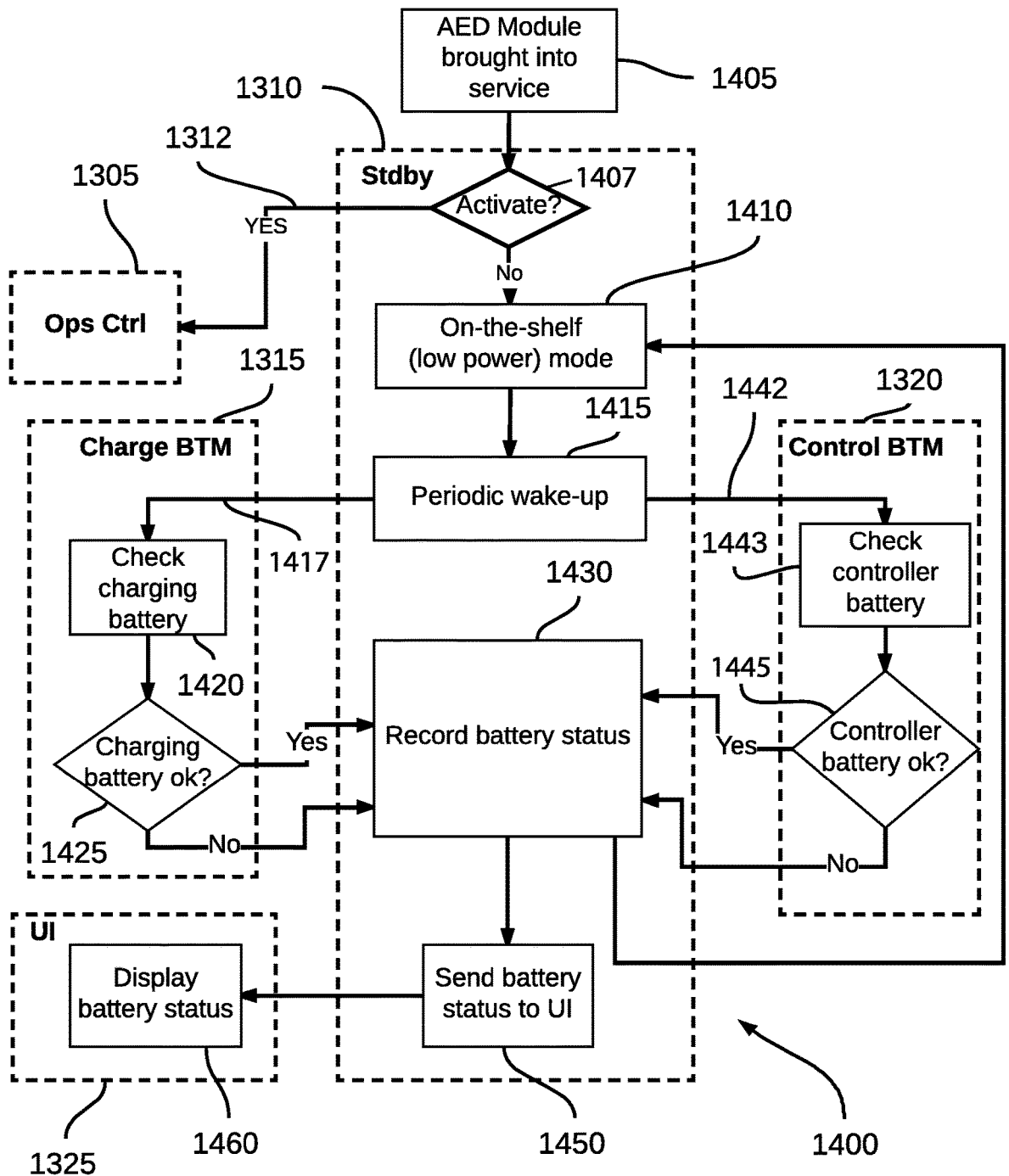
FIG. 14. Flowchart showing the firmware process for AED standby mode, in accordance with an embodiment.

FIG. 14 shows a standby process flow 1400 showing the firmware process for AED standby mode, in accordance with an embodiment. Standby process flow 1400 begins when the AED module is brought into service in a step 1405. This step may involve, for example, the insertion of a 9V battery into the appropriate receptacle, or the removal of an insulating strip from the battery compartment to bring the power source in contact with the rest of the internal circuitry. Then a decision 1407 is made to determine whether the AED is to be activated in the normal mode of operation. If the decision is YES, then Stdby 1310 sends standby signal 1312 to Ops Ctrl 1305 to commence normal, non-standby functions of AED module in service, as was also shown in FIG.

13. If decision 1407 is NO, then Stdby 1310 activates the AED module in an On-the-shelf (low power) mode in a step 1410.

While in low power mode, in the embodiment shown in FIG. 14, Stdby 1310 is activated on a preset schedule to check the status of the batteries in a periodic wake-up step 1415. In one aspect, a message 1417 is then sent to a step 1420 in Charge BTM 1315 to check the status of the household battery that is used to charge the capacitor (or multiple capacitors). A decision 1425 is made at Charge BTM 1315 to determine whether the charging battery status is okay (i.e., there is enough charge left in the charging battery to power the necessary therapeutic shock). Whether the charging battery status is YES okay or NO not okay, the battery status is recorded in a step 1430. Sequentially, or in parallel, a message 1442 is sent to a step 1443 in Control BTM 1320 to check the status of a separate battery that is used to power the control circuitry in the AED module, in accordance with an embodiment. A determination is made in a decision 1445 whether or not the controller battery status is okay and, whether the status is YES okay or NO not okay, the battery status is again recorded in step 1430. The status of both the charging battery and the controller battery are sent to UI 1325 in a step 1450, then displayed to the user in a step 1460.

Figure 15:
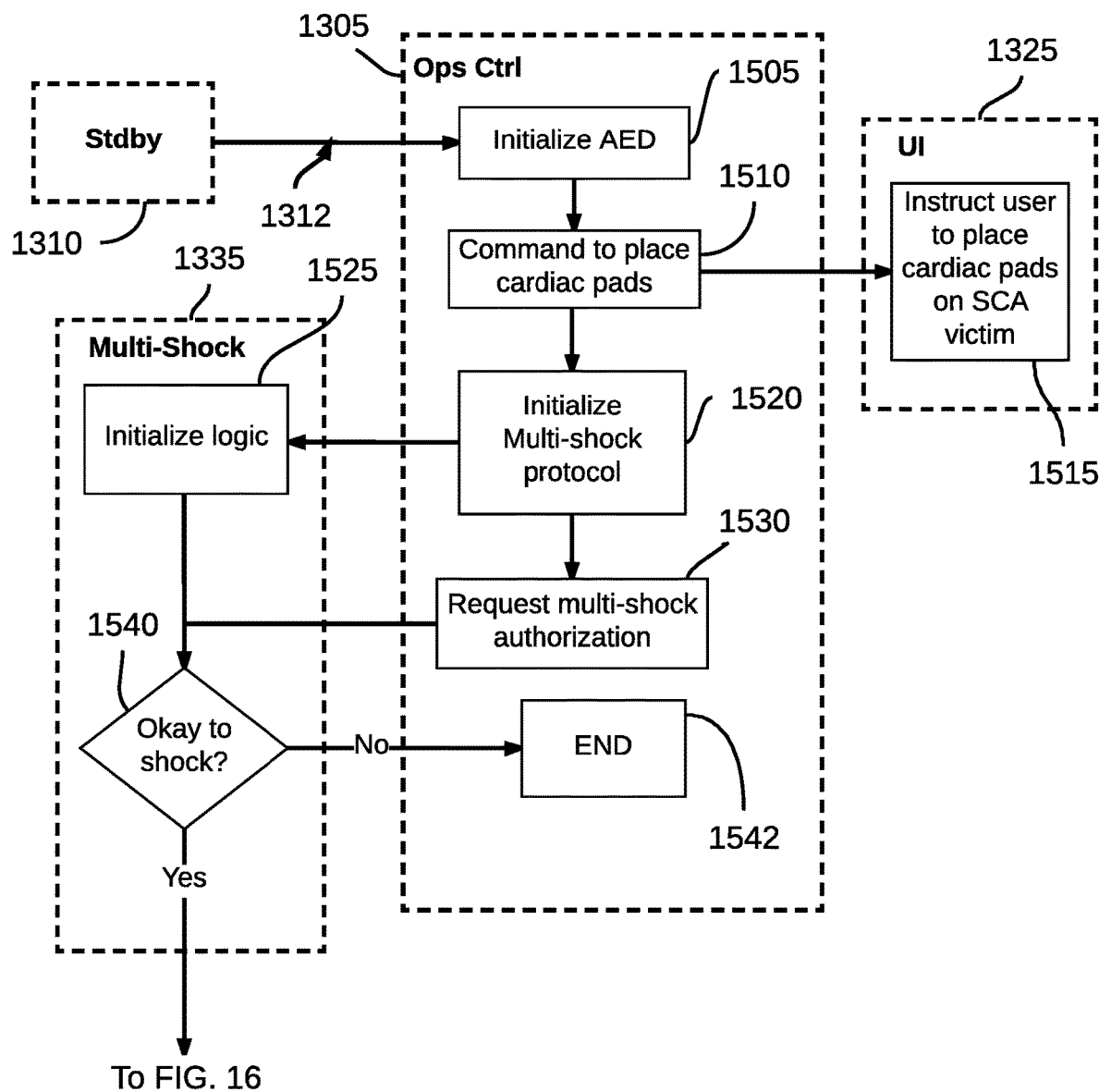
FIGS. 15-16. Flowchart showing the firmware process for administration of a shock protocol, in accordance with an embodiment.
Figure 16:
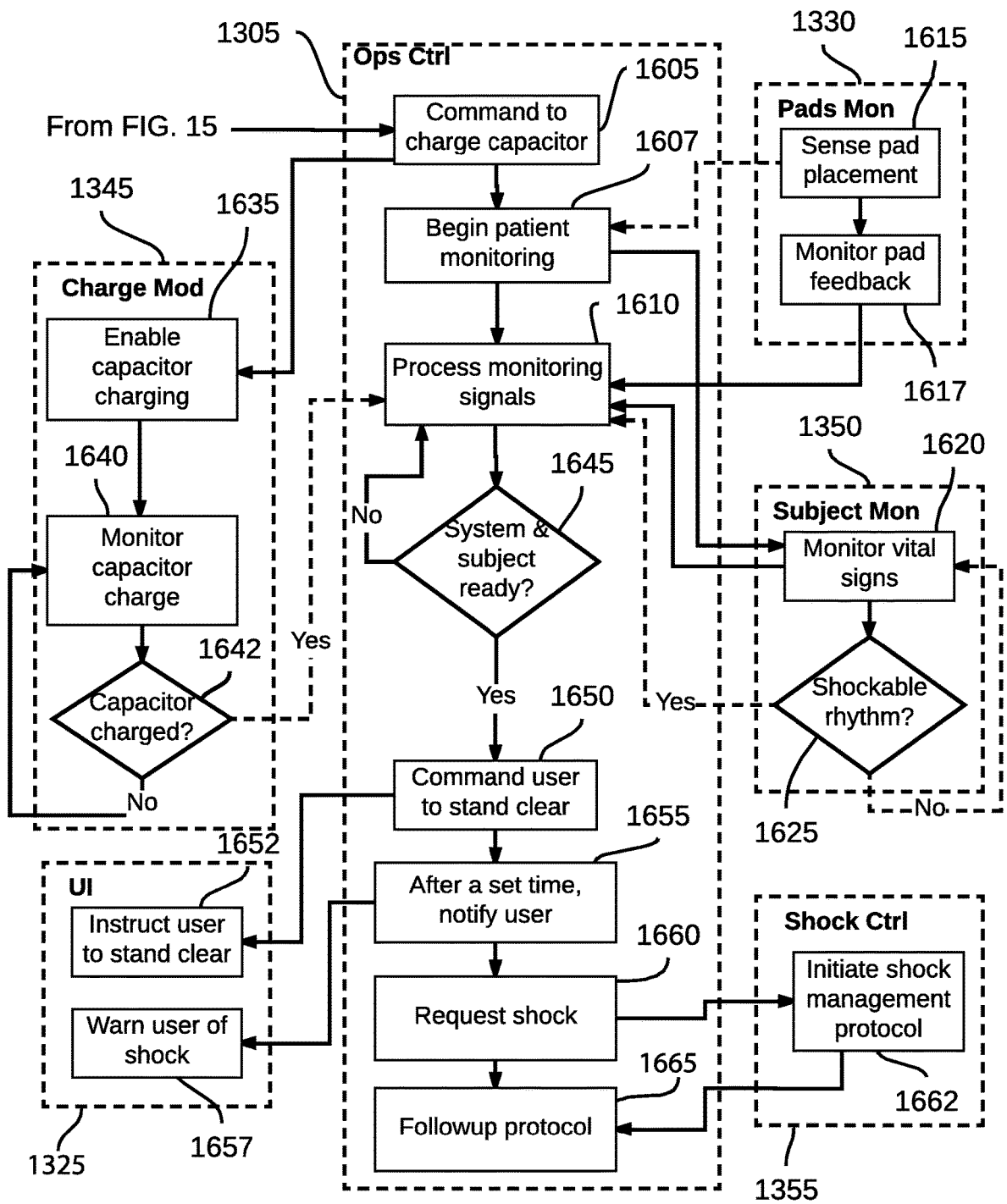

Considering now FIGS. 15 and 16, an exemplary embodiment of a process that is started when a signal 1312 to commence the shock protocol of the AED is illustrated. When signal 1312 is received at Ops Ctrl 1305, a step 1505 initializes the AED module for normal operation. In a step 1510, a command to place the cardiac pads on the SCA patient is sent to UI 1325, at which an indicator or display message instructs the user to place the cardiac pads, in a step 1515. Then, in a step 1520, a multi-shock protocol is initialized at Multi-Shock 1335, where "multi-shock" refers to the treatment protocol in which, if certain preset conditions are met, then a series of shocks can be generated at the AED module then applied to the SCA patient as needed. The initialization of the multi-shock protocol at Multi-Shock 1335 indicates to Multi-Shock 1335 the start of an emergency session involving an SCA patient, and that future requests for authorization to shock are related to this specific SCA patient. Then, in a step 1525, logic to control the number of allowed shocks is initialized at Multi-Shock 1335. The logic may include, for example, an analysis of the number of shocks already applied, and the current status of the physiological indicators measured from the SCA patient. In a step 1530, a request is made to Multi-Shock 1335 to request authorization to apply a shock. The logic within Multi-Shock 1335 analyzes the request and, in a decision 1540, determines whether to approve the generation and application of a shock to the SCA patient. If the answer to decision 1540 is NO, then the process is ended in a step 1542. If the answer to decision 1540 is YES, then the process moves back to Ops Ctrl 1305, as shown in FIG. 16.

Referring now to FIG. 16, a YES result of decision 1540 from Multi-Shock 1335 is communicated to Ops Ctrl 1305, at which a step 1605 issues a command to Charge Mod 1345 to charge the capacitor. At the same time, or sequentially, Ops Ctrl 1305 begins monitoring the patient in a step 1607. The monitoring involves, for example, sensing the cardiac pad placement on the SCA patient in a step 1615 at Pads Mon 1330. The feedback from the cardiac pads, such as the correct placement of the cardiac pads on the SCA patient, are monitored in a step 1617 at Pads Mon 1330, and the results are fed back to a step 1610 to process the various monitoring signals. Patient monitoring of step 1607 may also include monitoring the vital signs of the SCA patient in a step 1620 at Subject Mon 1350. The vital signs, such as cardiac rhythm, are fed back to step 1610 to be monitored. Additionally, Subject Mon 1350 also determines, in a decision 1625, whether or not the detected cardiac rhythm corresponds to a shockable rhythm, as previously described above. If the answer to decision 1625 is YES, then the result is communicated to step 1610 as part of the signal monitoring. If the answer to decision 1625 is NO, then Subject Mon 1350 returns to step 1620 to continue monitoring the vital signs.

In an embodiment, at Charge Mod 1345, a step 1635 enables the capacitor charging circuitry, and the capacitor charging status is monitored in a step 1640. A decision 1642 determines whether the capacitor has been sufficiently charged to enable the application of a shock to the SCA patient. If the answer to decision 1640 is YES, then the result is communicated to step 1610. If the answer to decision 1640 is NO, then Charge Mod 1345 returns to step 1640 to continue monitoring the capacitor charge status.

The monitored signals from step 1610 are then fed into a decision 1645 to determine whether both the charging system and the SCA patient are ready for the application of a shock. If the answer to decision 1645 is NO, then Ops Ctrl 1305 continues to monitor the incoming signals in step 1610. If the answer to decision 1645 is YES, then Ops Ctrl 1305 commands the user to stand clear of the SCA patient in a step 1650, which is communicated through UI 1325, which instructs the user to stand clear via a display message or other means in a step 1652. After a set time period, such as 5 to 10 seconds during which the user should have stood back from the SCA patient, Ops Ctrl 1305 warns the user in a step 1655 of the incoming shock, which is communicated to the user in a step 1657 at UI 1325. Ops Ctrl 1305 then requests a shock in a step 1660, which prompts Shock Ctrl 1355 to initiate a shock management protocol in a step 1662. Upon completion of the shock application, Ops Ctrl 1305 goes into a follow-up protocol step 1665.

Figure 17:
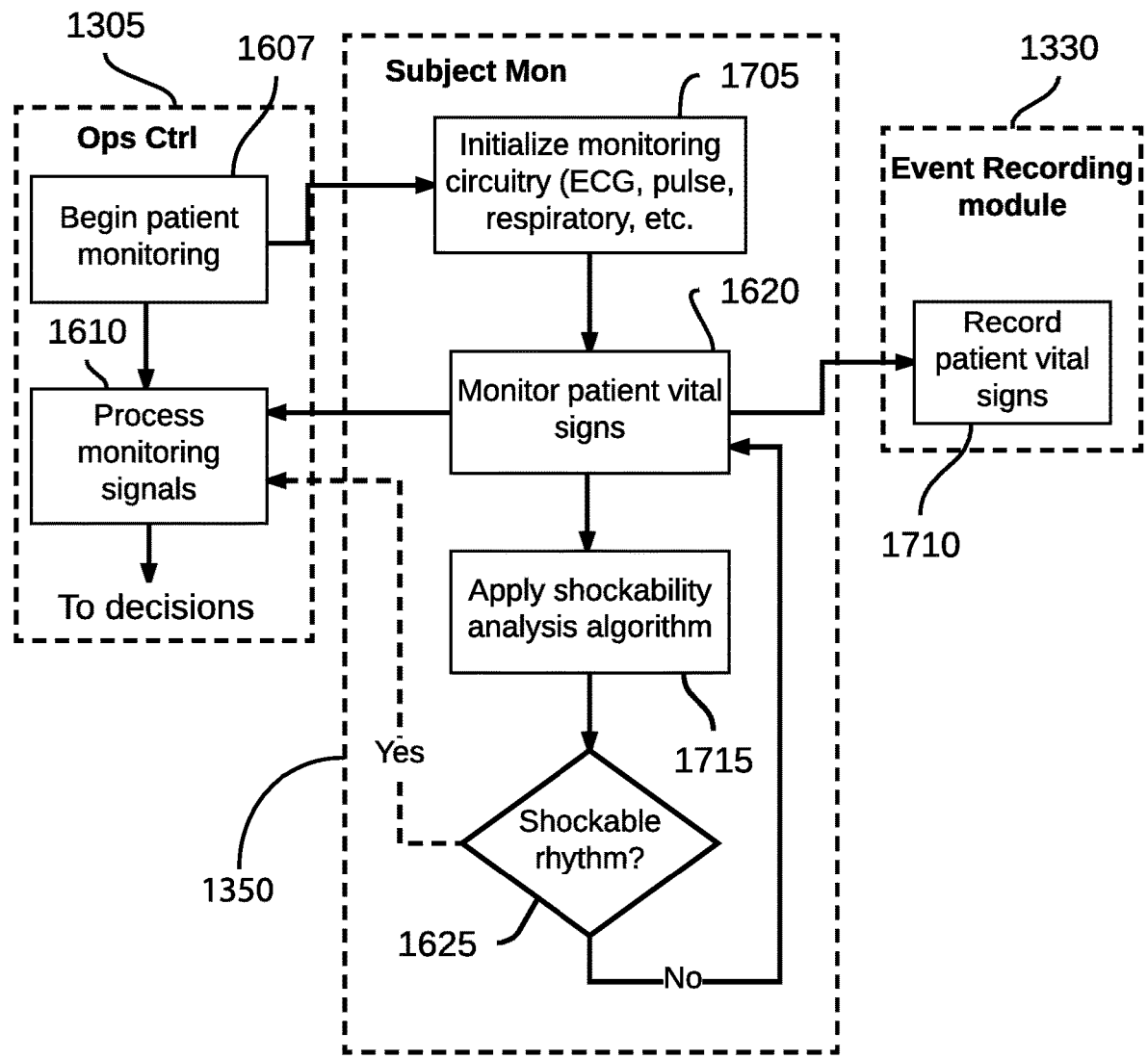
FIG. 17. Flowchart showing the firmware process for monitoring a SCA patient using the AED module, in accordance with an embodiment.

Turning now to FIG. 17, further details of the processing performed by Subject Mon 1350, in accordance with an embodiment, are described. Subject Mon 1350, as shown in FIGS. 16 and 17, receives a signal from Ops Ctrl 1305 to begin patient monitoring. When this signal is received at Subject Mon 1350, a step 1705 initializes the patient monitoring circuitry provided with the AED module. For example, sensors for electrocardiograph monitoring, cardiac rhythm monitoring, and respiratory rhythm can be included with the AED module. The various monitored signals are recorded in a step 1710 at Event Recording Module 1330, and also returned to Ops Ctrl 1305 to step 1610 of processing the various monitoring signals. The patient vital signs so measured are also fed into a step 1715 to apply a shockability analysis algorithm, as previously described, then to decision 1625 to determine whether the SCA patient is exhibiting a shockable cardiac rhythm.

Figure 18:
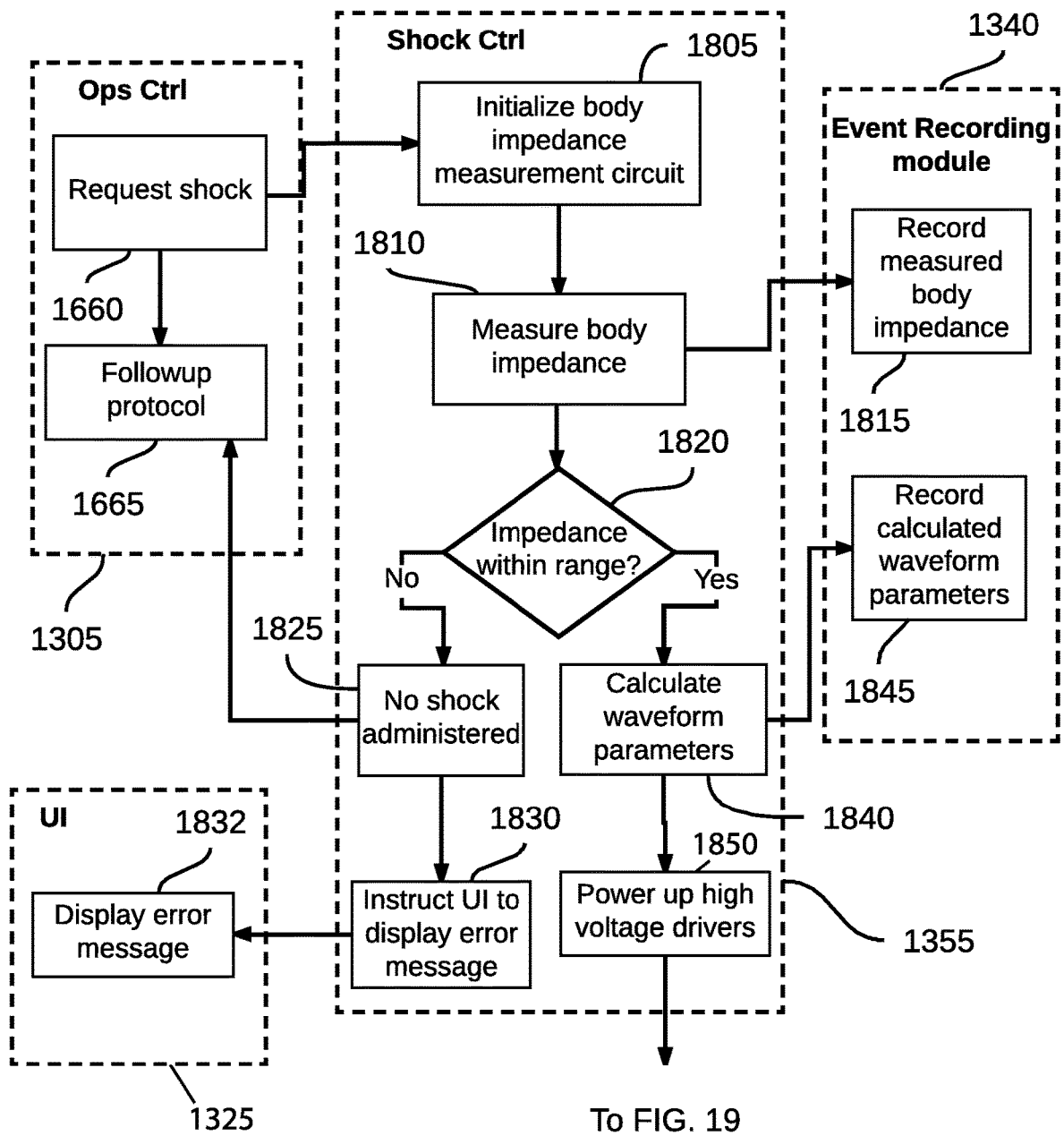
FIGS. 18-19. Flowchart showing the firmware process for managing a shock protocol and generating an electric shock, in accordance with an embodiment.
Figure 19:
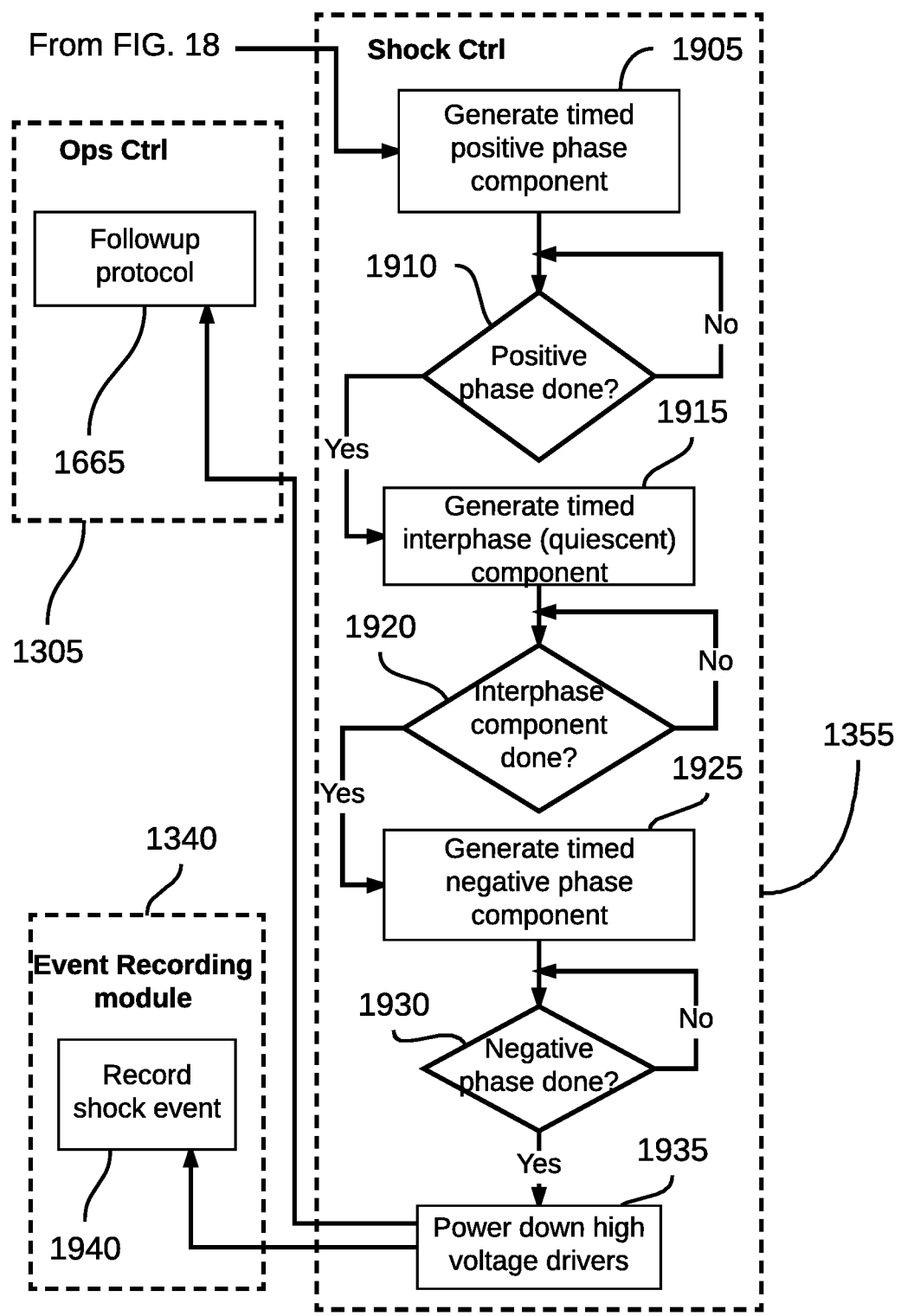

FIGS. 18 and 19 illustrate further details of step 1662 initiate shock management protocol as shown in FIG. 16, in accordance with an embodiment. The shock management protocol involves the firmware process for managing a shock protocol and generating an electric shock, in accordance with an embodiment. When Ops Ctrl 1305 requests a shock to be generated in step 1660, Shock Ctrl 1355 receives the request and initializes a body impedance measurement circuit in a step 1805. Then, using sensors in the cardiac pads, for example, or by other measurement mechanism provided with the particular embodiment of the AED module, the body impedance of the SCA patient is measured in a step 1810. The measured body impedance is recorded at Event Recording Module 1340 in a step 1815.

Continuing to refer to FIG. 18, a decision 1820 is made to determine whether the body impedance measured in step 1810 is within the range in which the AED module power circuitry can adjust the shock waveform for safe application to the particular patient. For instance, if a biphasic waveform, such as shown in FIG. 12 is to be used for the shock, there is a range of body impedance values for which the AED module is able to accommodate and adjust the waveform parameters for application of shock within American Heart Association guidelines. If the measured body impedance is lower (i.e., the SCA patient is too small) or higher (i.e., the SCA patient is too large) than the range of allowable body impedance values, then Ops Ctrl 1305 is so notified in a step 1825 and no shock is administered. Shock Ctrl 1355 then instructs UI 1325 to display an error message in a step 1830, and UI 1325 accordingly displays an error message for the user in a step 1832.

If decision 1820 determines that the measured body impedance is within the range for which a suitable waveform can be generated, then the necessary waveform parameters are calculated in a step 1840. Step 1840 involves, for example, uses an algorithm that, given vital sign measurements from the patient such as, but not limited to, body impedance, cardiac rhythm, and ECG data, calculates the appropriate timing and amplitudes of the positive and negative phases of the generated waveform, as shown in previously discussed FIG. 11. The calculated waveform parameters are recorded at Event Recording module 1340 in a step 1845, then instructions are sent to the high voltage drivers in the AED module to power up in a step 1850.

Referring now to FIG. 19, once the high voltage drivers are powered up in step 1850, Shock Ctrl 1355 instructs the high voltage drivers to generate a timed positive phase component of a biphasic waveform shock in a step 1905. Shock Ctrl 1355 monitors the generation of the timed positive phase component and, in a decision 1910, determines whether the generation of the timed positive phase component is complete. If decision 1910 determines that the high voltage drives have not completed the generation of the timed positive phase component, then Shock Ctrl 1355 continues to monitor the high voltage drivers. When the result of decision 1910 is YES, then Shock Ctrl 1355 instructs the high voltage drivers to generate the timed interphase, or quiescent, component between the positive and negative phases of the biphasic waveform in a step 1915. Again, Shock Ctrl 1355 monitors the generation of the timed interphase component and, in a decision 1920, determines whether the generation of the timed interphase component is complete. If decision 1920 determines that the timed interphase component generation is not yet complete, then Shock Ctrl 1355 continues to monitor the high voltage drivers. When the result of decision 1920 is YES, then Shock Ctrl 1355 instructs the high voltage drivers to generate the timed negative phase component in a step 1925. Yet again, Shock Ctrl 1355 monitors the generation of the timed negative phase component and, in a decision 1930, determines whether the generation of the timed negative phase component is complete. If decision 1930 determines that the timed negative phase component generation is not yet complete, then Shock Ctrl 1355 continues to monitor the high voltage drivers. When the result of decision 1930 is YES, then Shock Ctrl 1355 instructs the high voltage drivers to power down in a step 1935 and proceeds to the follow-up protocol at Ops Ctrl 1305. The details of the shock event are also recorded at Event Recording Module 1340 in a step 1940.

In another embodiment, the portable AED is configured to be housed in a bracket, which is mountable on a wall or other location. The bracket can include, for example, a connection to a power outlet such that the bracket can serve as a charging station for the AED, if a rechargeable battery is used within the AED module, or to provide additional functions. For instance, the bracket provides a monitoring function for the AED so as to alert the user, e.g., via a visual warning on the bracket or communication through the associated mobile device application or user webpage, in the case of situations such as: 1) the AED has been removed from the bracket; 2) a battery in the AED is low and needs to be replaced; and 3) the AED has a problem and needs to be serviced. The bracket can also include a button, either a physical button or on a touch screen, to immediately alert EMS or other contacts programmed into the mobile device application in the case of an emergency.

Figure 20:
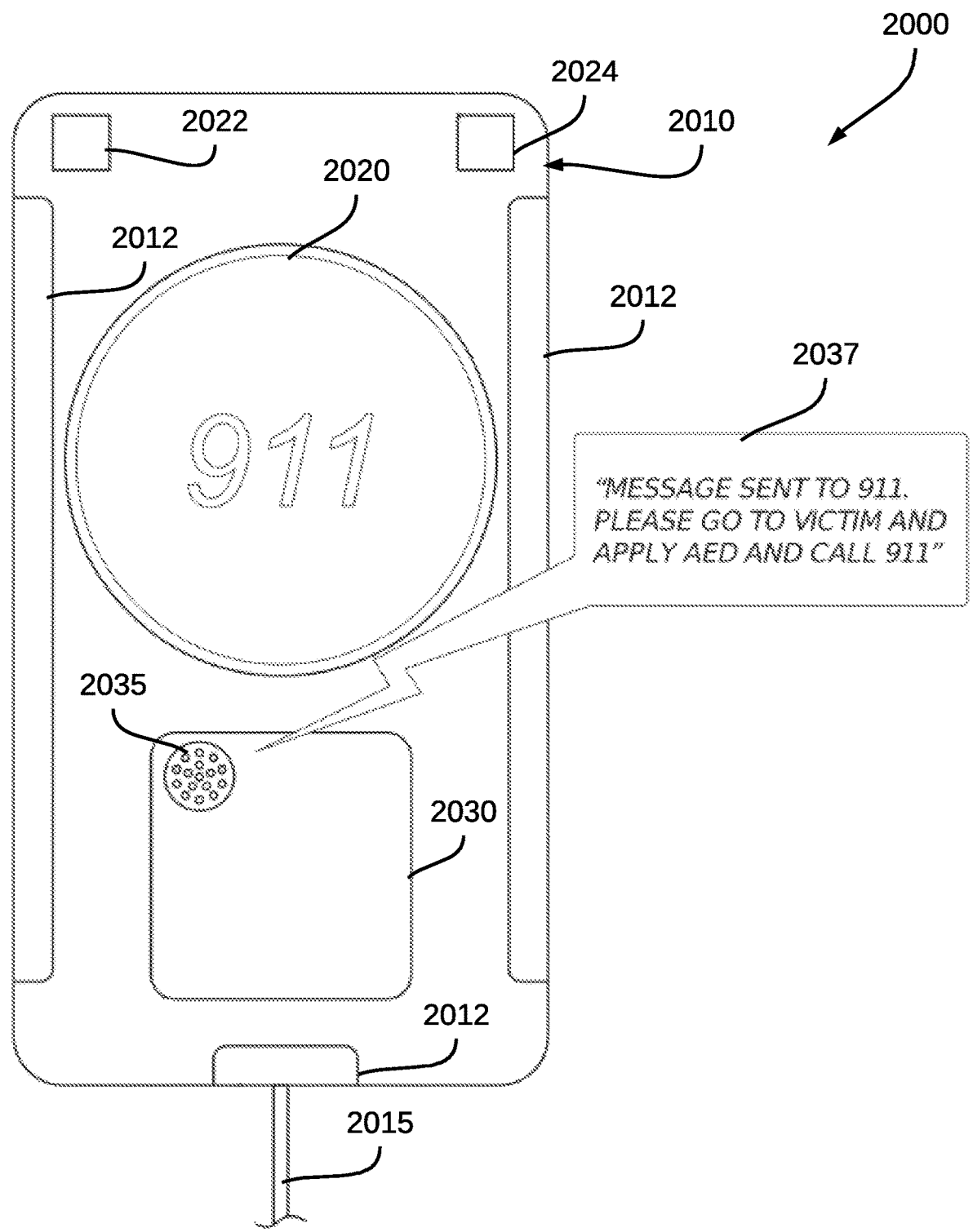
FIG. 20. Configuration of a bracket on which the AED module is mounted, in accordance with an embodiment.

An exemplary embodiment of a bracket is shown in FIG. 20. A bracket system 2000 includes a bracket body 2010, which in turn includes one or more lips 2012 (three are shown in the embodiment illustrated in FIG. 20) for housing an AED module (not shown) when the AED module is not in use. In the example shown in FIG. 20, bracket system 2000 includes an emergency call button 2020, which can be pressed by a user to immediately contact emergency medical services (e.g., via a 911 call in the US). Alternatively, call button 2020 can be replaced by a touchscreen including an emergency call function as well as being capable of displaying additional information, such as the AED battery status and AED user guidance. Call button 2020 (or a touchscreen equivalent) can also be configured to alert specified contacts programmed into a software application installed on a mobile device. For instance, the firmware in bracket system 2000 can be configured to automatically contact EMS as well as specified contacts (e.g., relatives and friends) programmed into the software application on a mobile device paired with bracket system 2000.

Bracket system 2000 also includes a sensor 2022 for detecting whether the AED module is housed in bracket body 2010. For instance, when the AED module is housed in bracket body 2010, sensor 2022 detects the presence of the AED module such that bracket system 2000 remains in a low power mode. When the AED module is removed from bracket system 2000, then bracket system 2000 goes into an active mode, in which certain functions of the bracket system 2000 are activated. Optionally, bracket system 2000 can be configured such that, when sensor 2022 detects that the AED module has been removed from bracket system 2000, bracket system 2000 automatically prompts the user to contact EMS or even immediately contact EMS without additional user input.

As shown in FIG. 20, bracket system 2000 also includes an indicator 2024, which can be used to show the user the status of a Wi-Fi connection or cellular signal strength, if bracket system 2000 is configured to be connectable to an external communication system. Bracket system 2000 also includes a microphone 2030 and a speaker 2035 to facilitate hands-free communications with EMS via bracket system 2000. For instance, when the AED module is removed from bracket system 2000, bracket system 2000 automatically alerts EMS that there is an emergency situation, and also prompts the user by audio (as shown in FIG. 20) or by visual prompt (e.g., if a touchscreen is used instead of emergency call button 2020). As an example, the removal of the AED module from bracket system 2000 leads to bracket system 2020 automatically contacting EMS and generating a voice prompt 2037 to the user. As an option, a lag time of, for instance, one minute may be given between the time the AED module is removed from bracket system 2000 to when EMS is contacted such that, if the AED module is accidentally removed, the user is given time to replace the AED module and avoid unnecessarily contacting EMS.

Figure 22:
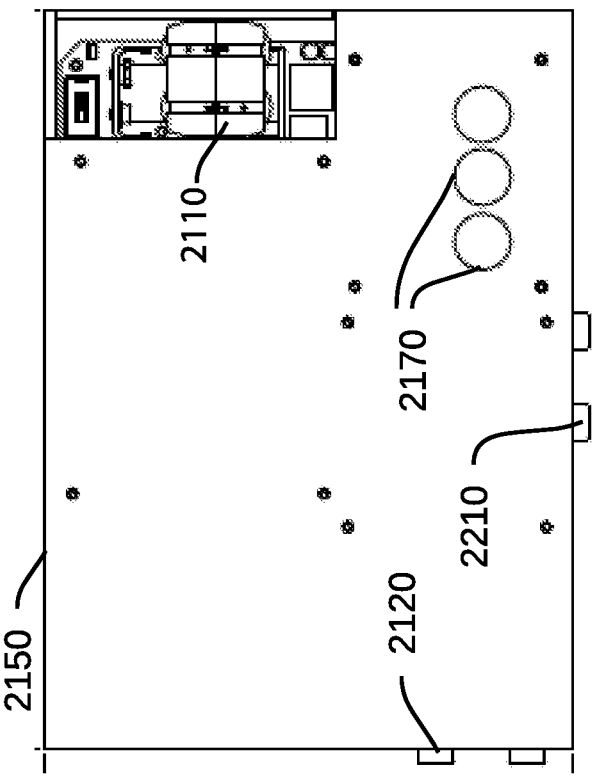
FIGS. 21-23. Iso, top, and side views of an exemplary AED module, in accordance with an embodiment.
Figure 23:
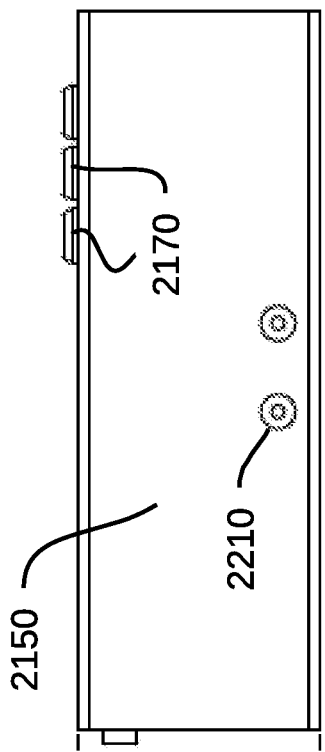
Figure 21:
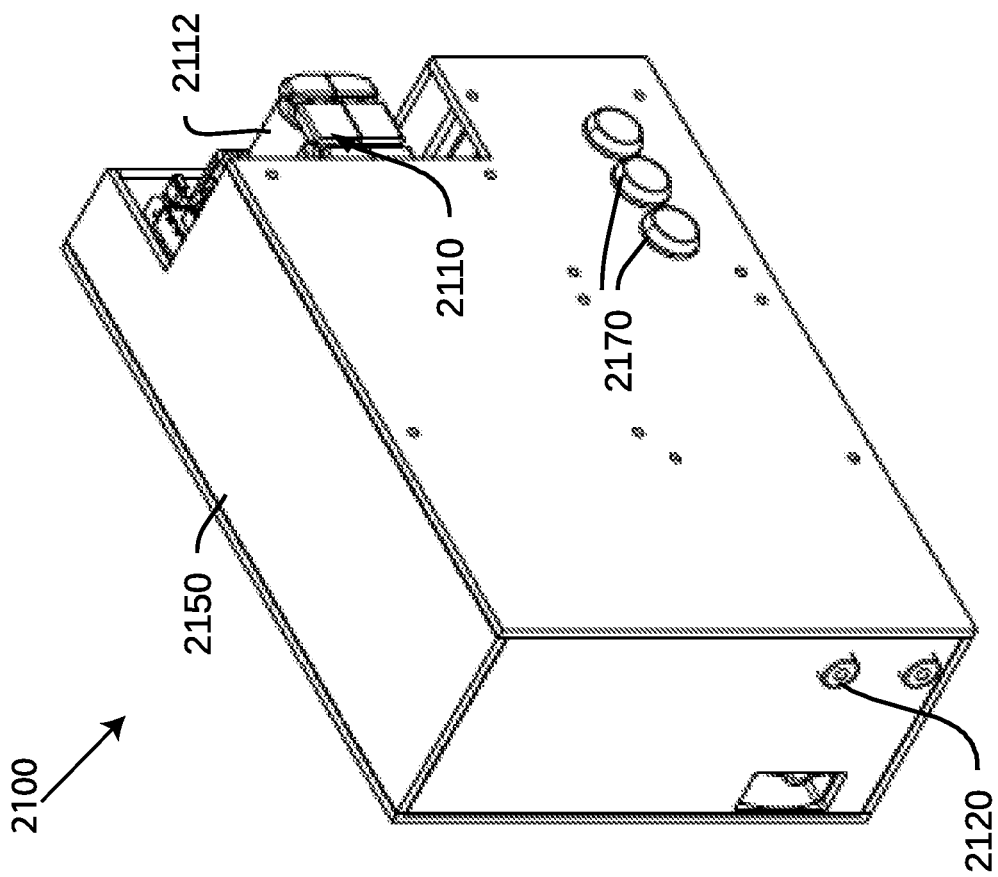

FIGS. 21-23 illustrate an exemplary embodiment of a portable AED module having features as described above. A portable AED module 2100 has dimensions of approximately 8-inches by 6-inches by 3-inches, and is shown in ISO, side, and bottom views in FIGS. 21-23, respectively. As shown in the exemplary embodiment, portable AED module 2100 is powered by a battery arrangement 2110 including a plurality of batteries 2112. In the embodiment shown in FIGS. 21-23, batteries 2112 are four CR123 batteries, which are commonly-available household batteries. AED module 2100 also include various connection ports 2120 and 2210 that provide connections for the cardiac pads, as well as test inputs and outputs. Outer enclosure 2150 of portable AED module 2100 is configured to minimize the risk of shock to the user, as well as to protect the internal electronic circuitry of the AED module from hazards, such as electrostatic discharge (ESD) and moisture. Portable AED module 2100 further includes a plurality of button switches 2170 for accessing various functionalities of portable AED module 2100, as well as serving as status indicators by color coded illumination of the button switches. Using a single household 9V alkaline battery, a high voltage of 1700V was achieved in 48 seconds, without current limiting, on the first charge cycle, and in 55 seconds, with current limiting for safety and battery power conservation. Embodiments replacing the 9V battery with four CR123 batteries in series have been demonstrated to achieve even faster charge times around 30 seconds using custom circuitry.

Figure 24:
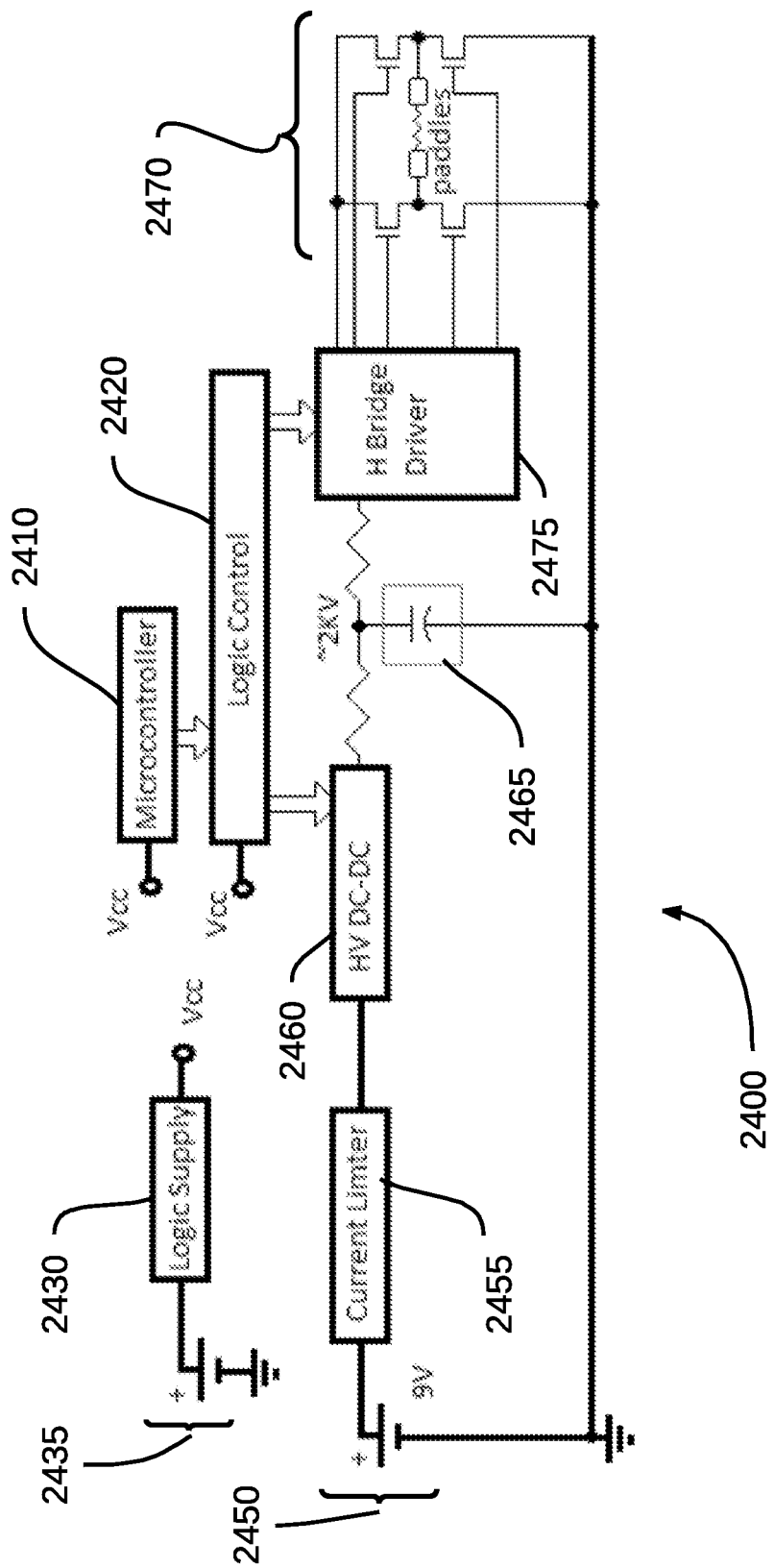
FIG. 24. An exemplary electronics architecture of an AED module, in accordance with an embodiment.

Turning now to FIG. 24, an example of an electronics architecture 2400 suitable for use with a portable AED module, in accordance with an embodiment, is shown. Electronics architecture 2400 includes a microcontroller 2410 (equivalent to microprocessor 20 of FIG. 2) overseeing the operations of a logic control circuit 2420. Power to microcontroller 2410 and logic control circuit 2420 are supplied via a logic supply circuit 2430 from a dedicated controller battery 2435, which is separate from a battery used to generate the therapeutic charge in the portable AED module, such that the controller operations do not drain the charge battery. The power source for the actual charge generation is a charge battery 2450, which is shown as a 9V battery in FIG. 24, although other types of household batteries can be used as well. A current limiter 2455 adjusts the current drawn from charge battery 2450 for the charge generation. Current from charge battery 2450 is directed through a high voltage DC-DC converter 2460, from which the output is used to charge a high voltage capacitor 2465. Logic control circuit 2420 provides the necessary logic for safely operating high voltage DC-DC converter 2460, as well as discharging high voltage capacitor 2465, if the generated charge is not needed or the operation of the portable AED module is interrupted. The charge stored in high voltage capacitor 2465 is output to the cardiac pads (shown in FIG. 24 as "paddles") via an H Bridge 2470 controlled by an H Bridge driver 2475, which in turn is controlled by logic control circuit 2420. H Bridge driver 2475 controls the generation of the appropriate shock waveform, such as a biphasic waveform, with the appropriate waveform parameters suitable for the specific SCA patient, as indicated by vital signs measurements. Electronics architecture 2400 is suitable for use, for example, with the firmware configuration described in relation to FIGS. 13-19.

The illustrations of arrangements described herein are intended to provide a general understanding of the structure of various embodiments, and they are not intended to serve as a complete description of all the elements and features of apparatus and systems that might make use of the structures described herein. Many other arrangements will be apparent to those of skill in the art upon reviewing the above description. Other arrangements may be utilized and derived therefrom, such that structural and logical substitutions and changes may be made without departing from the scope of this disclosure. Figures are also merely representational and may not be drawn to scale. Certain proportions thereof may be exaggerated, while others may be minimized. Accordingly, the specification and drawings are to be regarded in an illustrative rather than a restrictive sense.

In the foregoing specification, specific embodiments have been described. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of present teachings. The descriptive labels associated with the numerical references in the figures are intended to merely illustrate embodiments of the invention, and are in no way intended to limit the invention to the scope of the descriptive labels. The present systems, methods, means, and enablement are not limited to the particular systems, and methodologies described, as there can be multiple possible embodiments, which are not expressly illustrated in the present disclosures. It is also to be understood that the terminology used in the description is for the purpose of describing the particular versions or embodiments only, and is not intended to limit the scope of the present application.

Some embodiments, illustrating its features, will now be discussed in detail. The words "comprising," "having," "containing," and "including," and other forms thereof, are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise. Although any methods, and systems similar or equivalent to those described herein can be used in the practice or testing of embodiments, the preferred methods, and systems are now described. The disclosed embodiments are merely exemplary.

What is claimed is:

1. A compact, automated external defibrillator (AED) system, the system comprising:
  an electronics module, including:
    a power source,
    electronic circuitry for generating, storing, and dispensing electrical charge from the power source, the electrical charge being suitable for at least one electrical shock to be applied to a sudden cardiac arrest (SCA) patient,
    a display for providing guidance to a user of the system, the guidance including instructions on using the system, and a single microprocessor for controlling both the electronic circuitry and the display; and at least two cardiac pads, electrically connected with the electronics module and configured for external attachment to the SCA patient so as to transfer the at least one electrical shock from the electronics module to the SCA patient;

wherein each one of the at least two cardiac pads includes at least one sensor, the at least one sensor being configured for measuring a cardiac rhythm and a body impedance of the SCA patient onto whom the at least two cardiac pads have been attached;

wherein the power source is a household battery;

wherein the electronics module includes a current charger and a capacitor;

wherein the current charger uses a low current constant charge rate to charge the capacitor;

wherein the low current constant charge rate is controlled by a pulse-width modulation (PWM) signal from the single microprocessor;

wherein the power source includes four CR123 batteries; and wherein the PWM signal from the single microprocessor is adjustable to enable charging of the capacitor to a prescribed amount of energy within 45 seconds.

2. The system of claim 1, further comprising firmware configured for automatically adjusting waveform characteristics of the at least one electrical shock in accordance with the body impedance.

3. The system of claim 1, further comprising an interface for connecting the electronics module with a mobile communication device, wherein the interface is in communication with the microprocessor.

4. The system of claim 1, wherein the single microprocessor and the electronic circuitry are configured to start to charge as soon as the system is turned on.

5. The system of claim 1, wherein the PWM signal from the single microprocessor is provided to the current charger independent of any measurement by the at least one sensor.

6. The system of claim 1, wherein the PWM signal from the single microprocessor is adjustable to enable charging of the capacitor to a prescribed amount of energy within 60 seconds.

* * * * *